(12) United States Patent
Alcarazo et al.

(10) Patent No.: US 9,962,690 B2
(45) Date of Patent: May 8, 2018

(54) N-SUBSTITUTED PYRIDINIOPHOSPHINES, PROCESSES FOR THEIR PREPARATION AND THEIR USE

(71) Applicant: STUDIENGESELLSCHAFT KOHLE MBH, Muelheim an der Ruhr (DE)

(72) Inventors: Manuel Alcarazo, Muelheim an der Ruhr (DE); Christian Wille, Essen (DE); Hendrik Tinnermann, Hamm (DE)

(73) Assignee: STUDIENGESELLSCHAFT KOHLE MBH, Muelheim an der Ruhr (DE)

( * ) Notice: Subject to any disclaimer, the term of this patent is extended or adjusted under 35 U.S.C. 154(b) by 0 days. days.

(21) Appl. No.: 15/307,077

(22) PCT Filed: Apr. 21, 2015

(86) PCT No.: PCT/EP2015/058618
§ 371 (c)(1),
(2) Date: Oct. 27, 2016

(87) PCT Pub. No.: WO2015/165781
PCT Pub. Date: Nov. 5, 2015

(65) Prior Publication Data
US 2017/0050180 A1    Feb. 23, 2017

(30) Foreign Application Priority Data

Apr. 27, 2014    (EP) .................................... 14166125

(51) Int. Cl.
  C07F 9/28    (2006.01)
  C07F 15/00   (2006.01)
  B01J 31/24   (2006.01)
  C07F 9/58    (2006.01)
  C07C 2/66    (2006.01)
  C07C 67/30   (2006.01)
  C07D 311/04  (2006.01)

(52) U.S. Cl.
  CPC ....... B01J 31/2409 (2013.01); B01J 31/2404 (2013.01); C07C 2/66 (2013.01); C07C 67/30 (2013.01); C07D 311/04 (2013.01); C07F 9/587 (2013.01); C07F 15/0073 (2013.01); C07F 15/0093 (2013.01); B01J 2231/32 (2013.01); B01J 2231/324 (2013.01); B01J 2531/18 (2013.01); B01J 2531/822 (2013.01); B01J 2531/828 (2013.01); C07C 2531/24 (2013.01)

(58) Field of Classification Search
CPC .................................. C07F 9/28; C07F 15/00
USPC ....................................................... 546/2, 21
See application file for complete search history.

(56) References Cited

U.S. PATENT DOCUMENTS 4,940,787 A    7/1990 Drent

FOREIGN PATENT DOCUMENTS

EP    0 271 144 A2    6/1988

OTHER PUBLICATIONS

Omotowa, B.A. et al.: Triazine-based polyfluorinated triquarternary liquid salts: Synthesis, characterization, and application as solvents in Rhodium(I)-catalyzed hydroformylation of 1-octene. Organometallics, vol. 23, pp. 783-791, 2004.*

Carson, E. C. et al.: Dioxygen-initiated oxidation of heteroatomic substrates incorporated into ancillary pyridine ligands of carboxylate-rich Diiron(II) complexes.Inorg. Chem., vol. 45, pp. 837-848, 2006.*

* cited by examiner

*Primary Examiner* — Charanjit Aulakh
(74) *Attorney, Agent, or Firm* — Norris McLaughlin & Marcus, P.A.

(57) ABSTRACT

The present invention deals with the synthesis and applications of new cationic compounds being useful as metal ligands. Specifically, N-alkyl/aryl substituted pyridiniophosphines are prepared and used as ligands for transition metals. The so-obtained metal complexes and their use as catalysts in chemical synthesis is also described. It also worth mentioning that N-alkyl/aryl pyridiniophosphines can be synthesized through a short, scalable and highly modular route.

10 Claims, 7 Drawing Sheets

28; X = H; R = Me; R' = Ph
29; X = CF₃; R = Me; R' = Ph

30; X = H; R = Me; R' = Ph
31; X = H; R = Ph; R' = Ph
32; X = F; R = Me; R' = Ph
33; X = CF₃; R = Me; R' = Ph
34; X = CF₃; R = Et;
R' = 3,5-di(CF₃)Ph

N-SUBSTITUTED PYRIDINIOPHOSPHINES, PROCESSES FOR THEIR PREPARATION AND THEIR USE

This application is a 371 of International Patent Application No. PCT/EP2015/058618, filed Apr. 21, 2015, which claims foreign priority benefit under 35 U.S.C. § 119 of European Patent Application No. 14166125.6, filed Apr. 27, 2014, the disclosures of which patent applications are incorporated herein by reference.

The present invention deals with the synthesis and applications of new cationic compounds being useful as metal ligands. Specifically, N-alkyl/aryl substituted pyridiniophosphines are prepared and used as ligands for transition metals. The so-obtained metal complexes and their use as catalysts in chemical synthesis is also described. It also worth to mention that the inventive N-alkyl/aryl pyridiniophosphines can be synthesized through a short, scalable and highly modular route.

For the design of an effective metal catalysed process, the choice of the ancillary ligand is crucial; in fact, it can be as critical as the choice of the metal itself. This is due to the extraordinary control that ligands exert over the reactivity of the resulting catalysts and, not less important, over the product selectivity of the catalysed process. The selection of the most appropriate ligand for each particular transformation must then consider among others, the nature of the rate determining step and the plausible (not desired) reaction pathways.

In this context where ligands that depict different properties are necessary, phosphanes play a prominent role because both, their donor ability and steric requirements can be adjusted by modification of the substituents attached to the phosphorus atom.

Very recently, the inventors have developed an alternative strategy for the synthesis of even weaker electron donor phosphines consisting on the direct attachment of up to three cationic bis(dialkylamino) cyclopropenium substituents to the central P-atom. The positive charges thus introduced account for the poor σ-donor and excellent π-acceptor abilities that these ligands depict. However, the specific use of di(isopropylamino) cyclopropenium substituents compromise to some extend the independent fine tune of steric and electronic properties of the resulting phosphines due to the synthetic and geometric restrictions that these cationic groups impose. Moreover, the best catalytic performances are often obtained by the employment of di- or tri-cationic catalysts that, because of their highly charged nature, depict low solubility in typical organic solvents. For these reasons, the use of alternative positive charged substituents, more amenable to stereoelectronic modification, seems to be adequate to further expand the still limited repertoire of extreme π-acceptor ligands and their applications in metal catalysis.

Now, the inventors have found out that N-(alkyl/arylpyridinium) substituted phosphines can be a potentially very useful family of strong π-acceptor ligands. According to the considerations of the inventors this is due to the simultaneous confluence of three beneficial factors: (a) the low-lying π* orbitals of the pyridinium moiety should effectively interact with the lone pair at phosphorus making the resulting phosphines very poor donating ligands; (b) besides the selection of the other two R-groups at phosphorus, the introduction of substituents on the pyridinium ring provides an additional manifold for the fine stereoelectronic tuning of the resulting phosphine (FIG. 1); and finally, (c) the reaction of 1-alkyl/aryl-2-chloro pyridinium salts with different secondary phosphines offers a short, effective and highly modular synthetic route to the target ligands.

Thus, the present inventions is directed to N-alkyl/aryl-substituted pyridiniophosphines having the general formula (I)

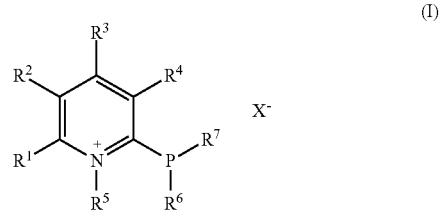

wherein
$R^1$, $R^2$, $R^3$ and $R^4$ are identical or different and each represent hydrogen, halogen, a linear, cyclic or branched $C_1$-$C_{20}$-alkyl, -alkenyl group or -alkynyl group or $C_5$-$C_{14}$-aryl or -heteroaryl group, which can have suitable substituents selected from halogen, =O, —OH, —OR, —NH$_2$, —NHR, —NR$_2$, aryl or heteroaryl, or at least one of $R^1$, $R^2$, $R^3$ and $R^4$ is bound to the pyridinio ring via —O— or —NR—, or at least two of $R^1$, $R^2$, $R^3$ and $R^4$ can form a linear or branched $C_4$ to $C_{12}$ alkyl ring, which can comprise at least one unsaturated bond and which can have suitable substituents selected from halogen, =O, —OH, —OR, —NH$_2$, —NHR, —NR$_2$, aryl or heteroaryl, or at least two of $R^1$, $R^2$, $R^3$ and $R^4$ can form a $C_5$ to $C_{14}$-aromatic or -heteroaromatic ring which can have suitable substituents selected from halogen, —OH, —OR, —NH$_2$, —NHR, —NR$_2$, aryl or heteroaryl;

$R^5$ represents a linear, cyclic or branched $C_1$-$C_{20}$-alkyl group or $C_5$-$C_{14}$-aryl or -heteroaryl group, which can have suitable substituents selected from halogen, =O, —OH, —OR, —NH$_2$, —NHR, —NR$_2$, aryl or heteroaryl;

$R^6$ and $R^7$ each represent a saturated or unsaturated, linear, branched or cyclic $C_1$ to $C_{20}$-alkyl group or $C_5$-$C_{14}$-aryl or -heteroaryl group, which can have suitable substituents selected from halogen, —OH, —OR, —NH$_2$, —NHR, —NR$_2$, aryl or heteroaryl; or $R^6$ and $R^7$ can form a $C_4$ to $C_{20}$ ring which can comprise at least one unsaturated bond or an aromatic or heteroaromatic ring which can have suitable substituents selected from halogen, —OH, —OR, —NH$_2$, —NHR, —NR$_2$, aryl or heteroaryl;

R represents a $C_1$-$C_{20}$-alkyl group or $C_5$-$C_{14}$-aryl or -heteroaryl group which can have suitable substituents selected from halogen, —OH, —OR, —NH$_2$, —NHR, —NR$_2$, aryl or heteroaryl, and X$^-$ is an anion.

$R^1$, $R^2$, $R^3$, $R^4$ $R^5$, $R^6$ and $R^7$ and optional substituents thereof are such that they do in particular not negatively influence the reactivity of the pyridinio compound or of the metal complexes thereof. Thus, any reactive substituent such as e.g. —OH of any of $R^1$, $R^2$, $R^3$, $R^4$ $R^5$, $R^6$ and $R^7$ should preferably be not on the carbon atom attached to a pyridinio ring atom. Substituents such as —O—, —NH or NR— might be present in the $C_1$-$C_{20}$-alkyl group of $R^1$, $R^2$, $R^3$, $R^4$ $R^5$, $R^6$, $R^7$ and R and might thus also form ether linkages or amino linkages.

In a particular embodiment, the present invention concerns N-substituted pyridiniophosphines of the general formula (I), wherein $R^1$, $R^3$ and $R^4$ each represent hydrogen and $R^2$ represents, halogen, a linear, cyclic or branched $C_1$-$C_{20}$-alkyl, -alkenyl group or -alkynyl group or $C_5$-$C_{14}$-aryl or -heteroaryl group, which can have suitable substituents selected from halogen, =O, —OH, —OR, —NH$_2$, —NHR, —NR$_2$, aryl or R$^2$ is bound to the pyridinio ring via —O— or —NR—; and R$^5$, R$^6$, R$^7$, R and X$^-$ have the meaning as given before.

In the inventive N-substituted pyridiniophosphine of the general formula (I), X$^-$ can be any anion which does not adversely affect the catalysed reaction and can be Cl$^-$, Br$^-$, I$^-$, PF$_6^-$, SbF$_6^-$, BF$_4^-$, ClO$_4^-$, F$_3$CCOO$^-$, Tf$_2$N$^-$, (Tf=trifluoromethanesulfonyl), TfO$^-$, tosyl, [B[3,5-(CF$_3$)$_2$C$_6$H$_3$]$_4$]$^-$, [B(C$_6$F$_5$)$_4$]$^-$, [Al(OC(CF$_3$)$_3$)$_4$]$^-$, and preferably an anion selected from BF$_4^-$, PF$_6^-$, SbF$_6^-$, [B(C$_6$F$_5$)$_4$]$^-$.

The present invention is also directed to the process for the preparation of N-substituted pyridiniophosphine with the general formula I:

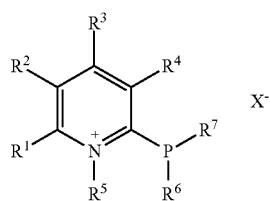

(I)

wherein

R$^1$, R$^2$, R$^3$ and R$^4$ are identical or different and each represent hydrogen, halogen, a linear, cyclic or branched C$_1$-C$_{20}$-alkyl, -alkenyl group or -alkynyl group or C$_5$-C$_{14}$-aryl or -heteroaryl group, which can have suitable substituents selected from halogen, =O, —OH, —OR, —NH$_2$, —NHR, —NR$_2$, aryl or heteroaryl, or at least one of R$^1$, R$^2$, R$^3$ and R$^4$ is bound to the pyridinio ring via —O— or NR—, or at least two of R$^1$, R$^2$, R$^3$ and R$^4$ can form a linear or branched C$_4$ to C$_{12}$ alkyl ring, which can comprise at least one unsaturated bond and which can have suitable substituents selected from halogen, =O, —OH, —OR, —NH$_2$, —NHR, —NR$_2$, aryl or heteroaryl, or at least two of R$^1$, R$^2$, R$^3$ and R$^4$ can form a C$_5$ to C$_{14}$-aromatic or -heteroaromatic ring which can have suitable substituents selected from halogen, —OH, —OR, —NH$_2$, —NHR, —NR$_2$, aryl or heteroaryl;

R$^5$ represents a linear, cyclic or branched C$_1$-C$_{20}$-alkyl group or C$_5$-C$_{14}$-aryl or -heteroaryl group, which can have suitable substituents selected from halogen, =O, —OH, —OR, —NH$_2$, —NHR, —NR$_2$, aryl or heteroaryl;

R$^6$ and R$^7$ each represent a saturated or unsaturated, linear, branched or cyclic C$_1$ to C$_{20}$-alkyl group or or C$_5$-C$_{14}$-aryl or heteroaryl group, which can have suitable substituents selected from halogen, —OH, —OR, —NH$_2$, —NHR, —NR$_2$, aryl or heteroaryl; or R$^6$ and R$^7$ can form a C$_4$ to C$_{20}$ ring which can comprise at least one unsaturated bond or an aromatic or heteroaromatic ring which can have suitable substituents selected from halogen, —OH, —OR, —NH$_2$, —NHR, —NR$_2$, aryl or heteroaryl;

R represents a C$_1$-C$_{20}$-alkyl group or C$_5$-C$_{14}$-aryl or -heteroaryl group which can have suitable substituents selected from halogen, =O, —OH, —OR, —NH$_2$, —NHR, —NR$_2$, aryl or heteroaryl, and X$^-$ is an anion
in which process a pyridinio-compound salt with the general formula II:

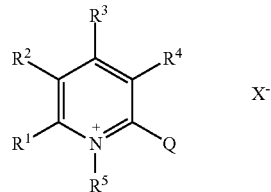

(II)

wherein R$^1$, R$^2$, R$^3$, R$^4$, R$^5$ and X$^-$ are defined as above and Q represents a leaving group, is reacted with a phosphine of the general formula III:

HPR$^6$R$^7$ (III)

in which R$^6$ and R$^7$ are defined as above.

The leaving group Q can be chosen in a broad range and can be a halogen, sulfonate, tosyl or a triflate group.

The reaction conditions are not critical and basically comprise heating with gentle heat to reflux in an organic solvent such as THF of suspensions containing a pyridinium compound of general formula II (1.0 equiv.) with the desired secondary phosphine (2.5-3.0 equiv.) for 1 to 7 days. For sterically demanding substrates, microwave heating (150° C.) of the reaction mixtures might be used.

The new N-substituted pyridiniophosphines of the general formula (I) thus prepared can serve as ligands for metal complexes. They can be easily prepared by reacting the N-substituted pyridiniophosphines of the general formula (I) with a the desired metal precursors. As illustrative example, complexes containing B, Cu, Fe, Ni, Co, Ag, Au, Ru, Rh, Pd, Os, Ir and Pt have been prepared.

Thus, the present invention also concerns such metal complex of the general formula (IV)

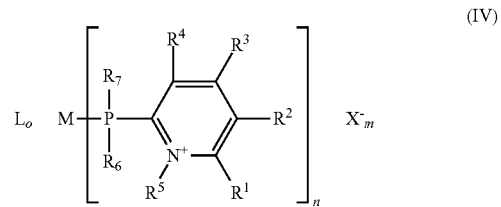

(IV)

wherein

R$^1$, R$^2$, R$^3$ and R$^4$ are identical or different and each represent hydrogen, halogen, a linear, cyclic or branched C$_1$-C$_{20}$-alkyl, -alkenyl group or -alkynyl group or C$_5$-C$_{14}$-aryl or -heteroaryl group, which can have suitable substituents selected from halogen, =O, —OH, —OR, —NH$_2$, —NHR, —NR$_2$, aryl or heteroaryl, or at least one of R$^1$, R$^2$, R$^3$ and R$^4$ is bound to the pyridinio ring via —O— or —NR—, or at least two of R$^1$, R$^2$, R$^3$ and R$^4$ can form a linear or branched C$_4$ to C$_{12}$ alkyl ring, which can comprise at least one unsaturated bond and which can have suitable substituents selected from halogen, =O, —OH, —OR, —NH$_2$, —NHR, —NR$_2$, aryl or heteroaryl, or at least two of R$^1$, R$^2$, R$^3$ and R$^4$ can form a C$_5$ to C$_{14}$-aromatic or -heteroaromatic ring which can have suitable substituents selected from halogen, —OH, —OR, —NH$_2$, —NHR, —NR$_2$, aryl or heteroaryl;

R$^5$ represents a linear, cyclic or branched C$_1$-C$_{20}$-alkyl group or C$_5$-C$_{14}$-aryl or -heteroaryl group, which can have suitable substituents selected from halogen, =O, —OH, —OR, —NH$_2$, —NHR, —NR$_2$, aryl or heteroaryl;

$R^6$ and $R^7$ each represent a saturated or unsaturated, linear, branched or cyclic $C_1$ to $C_{20}$-alkyl group or $C_5$-$C_{14}$-aryl or -heteroaryl group, which can have suitable substituents selected from halogen, —OH, —OR, —NH$_2$, —NHR, —NR$_2$, aryl or heteroaryl; or $R^6$ and $R^7$ can form a $C_4$ to $C_{20}$ ring which can comprise at least one unsaturated bond or an aromatic or heteroaromatic ring which can have suitable substituents selected from halogen, —OH, —OR, —NH$_2$, —NHR, —NR$_2$, aryl or heteroaryl;

R represents a $C_1$-$C_{02}$-alkyl group or $C_5$-$C_{14}$-aryl or -heteroaryl group which can have suitable substituents selected from halogen, =O, —OH, —OR, —NH$_2$, —NHR, —NR$_2$, aryl or heteroaryl, and $X^-$ is an anion, M represents a metal atom, preferably chosen from the group consisting of B, Cu, Fe, Ni, Co, Ag, Au, Ru, Rh, Pd, Os, Ir and Pt.

L represents a ligand which can be cationic, anionic or neutral and all the same or different if more than one L is coordinated to the metal, and m can be 1, 2 or 3, n can be 1, 2 or 3, o can be an integer from 1 to 5, and m, n and o are chosen, depending on the metal atom, to obtain a metal complex which is stable and can serve as catalyst in various chemical reactions as detailed below.

Depending on the metal selected from B, Cu, Ag, Fe, Ni, Co, Au, Ru, Rh, Pd, Os, Ir or Pt, the number of ligands L, of the inventive N-substituted pyridiniophosphines of the general formula (I) and of the anions $X^-$ is chosen to obtain a stable uncharged metal complex.

Ligands L on the metal complex can be chosen among halogen, CN, CO, alkenes, cycloalkenes and/or alkynes, arenes, nitriles, phosphines, amines, pyridines or carboxylates.

The metal complex preferably comprises M being selected from B, Cu, Ag, Fe, Ni, Co, Au, Ru, Rh, Pd, Os, Ir or Pt.

The inventive metal complexes can be advantageously used as catalysts in organic synthesis, in particular for cycloisomerizations and hydroarylations, but also for hydroxylation and hydroamination of unsaturated compounds such as alkynes, allenes and alkenes and direct arylation reactions.

The reaction conditions for the catalysed process are not critical quite soft and generally comprise stirring of the catalysts and the desired substrate in an organic solvent or mixtures thereof, such as dichloroethane, at moderate temperatures (20°. to 80° C.).

In the inventive compounds, one or more heteroatoms might be present as heterosubstituents which can have the meaning of halogen, =O, —OH, —OR, —NH$_2$, —NHR, —NR$_2$ as detailed above. Thus, a substituents group might also contain one to three halogen atoms such as a —CF$_3$. group Furthermore, $C_1$-$C_{20}$-alkyl can be straight chain or branched and can have 1, 2, 3, 4, 5, 6, 7, 8, 9, 10, 11, 12, 13, 14, 15, 16, 17, 18, 19 or 20 carbon atoms. Alkyl might be $C_1$-$C_{12}$-alkyl or lower alkyl such as $C_1$-$C_6$-alkyl, in particular methyl, ethyl, propyl, isopropyl, butyl, isobutyl, sec-butyl or tert-butyl, likewise pentyl, 1-, 2- or 3-methylpropyl, 1,1-, 1,2- or 2,2-dimethylpropyl, 1-ethylpropyl, hexyl, 1-, 2, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl. Substituted alkyl groups are trifluoromethyl, pentafluoroethyl and 1,1,1-trifluoroethyl.

Cycloalkyl might preferably be $C_3$-$C_{10}$-alkyl and may be cyclopropyl, cyclobutyl, cyclopentyl, cyclohexyl or cycloheptyl.

Alkenyl might be $C_2$-$C_{20}$ alkenyl. Alkynyl might be $C_2$-$C_{20}$ alkynyl.

Halogen is F, Cl, Br or I.

Alkoxy is preferably $C_2$-$C_{10}$ alkoxy such as methoxy, ethoxy, propoxy, iso-propoxy, tert-butoxy etc.

Heterocycloalkyl having one or more heteroatoms selected from among N, O and S is preferably 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl.

Optionally substituted means unsubstituted or monosubstituted, disubstituted, trisubstituted, tetrasubstituted, pentasubstituted, or even further substituted for each hydrogen on the hydrocarbon.

Aryl might be phenyl, naphthyl, biphenyl, anthracenyl, and other polycondensed aromatic systems.

Aryl-($C_1$-$C_6$)-alkyl might be benzyl or substituted benzyl.

Heteroaryl may have one or more heteroatoms selected from among N, O and S is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, also preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-Indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, also preferably 1,3-benzodioxol-5-yl, 1,4-benzodioxan-6-yl, 2,1,3-benzothiadiazol-4- or -5-yl or 2,1,3-benzoxadiazol-5-yl.

As illustrated in the Experimental Part below, the inventors have prepared pyridinium-substituted phosphines 12-19 in good to excellent yields through a two-steps sequence as shown in the Figures and Reaction Schemes in order to put their design concept into practice. First, N-alkylation of readily available 2-chloropyridines 1-4 with trimethyl- or triethyloxonium tetrafluoroborates afforded the corresponding pyridinium salts 6, 8-11 in excellent yields. 1-Aryl substituted 2-chloropyridinium salts such as 7 could be also obtained by an alternative procedure consisting on an Ullmann coupling between pyridone and iodoarenes followed by treatment with oxalyl chloride. Subsequently, the unprecedented condensation of 2-chloropyridinium salts 6-11 with a range of secondary phosphines efficiently afforded the desired pyridinium substituted phosphines 12-19 in moderate to good yields (see Scheme 1).

At this point the inventors tried to evaluate the donor endowment of the new cationic phosphines by analysis of the CO stretching frequencies in trans-[RhCl(CO)L$_2$] complexes 20-25 (Table 1 and Scheme 2). However, these data were misleading and certainly should be taken with caution. For example, the formal introduction of four —CF$_3$ groups in 16 seems to make the resulting ligand 19 a stronger neat donor (Table 1, Entries 3 and 6). This clearly indicates that in Rh complexes 20-25, the CO stretching frequencies may not be only determined by the electronic properties of the ligands on Rh, but also influenced by through-space interactions between CO and the other ligands or small geometric changes around the metal due to steric factors. For this reason the oxidation potential E, (ox) of phosphines 12-19, determined by cyclic voltammetry, was chosen as a more reliable parameter to rank their electronic properties. These data followed the expected tendency and suggest that ligands 17 and 18, both decorated with two cyclohexyl substituents, depict donor abilities similar to that of (MeO)$_3$P while 12, 15, 16 and 19 are even weaker donors than phosphites (Table 1).

TABLE 1

Carbonyl stretching frequencies in [RhCl(CO)L$_2$](BF$_4$)$_2$ complexes in the solid state and electrochemical redox potential of the ligands. The values of commonly used phosphorus ligands are also included for comparison.

| Entry | Ligand | $\tilde{v}_{CO}^{[a]}$ [RhCl(CO)L$_2$](BF$_4$)$_2$ | $E_p$ ox[b] |
|---|---|---|---|
| 1 | 12 | 1996 | 1.398 |
| 2 | 15 | 1994 | 1.355 |
| 3 | 16 | 2004 | 1.436 |
| 4 | 17 | 1982 | 1.297 |
| 5 | 18 | 1974 | 1.269 |
| 6 | 19 | 2001 | 1.578[c] |
| 7 | 26 | 1971 | 1.207 |
| 8 | 27 | — | 1.541 |
| 9 | Ph$_3$P | 1979 | 0.687 |
| 10 | (MeO)$_3$P | 2011 | 1.287 |

[a]Values in cm$^{-1}$.
[b]Oxidation peak potentials reported in V. Calibrated versus ferrocene/ferrocenium (E$_{1/2}$ = 0.24 V), Bu$_4$NPF$_6$ (0.1M) in CH$_2$Cl$_2$.
[c]measured in CH$_3$CN.

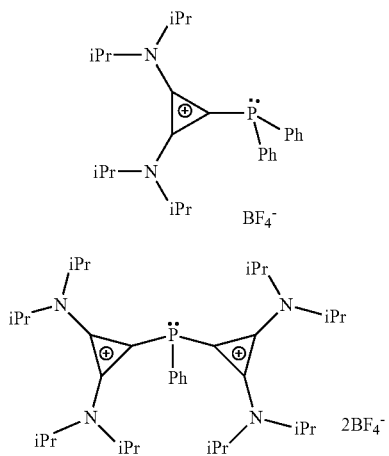

The E$_p$ (ox) values measured for cyclopropenium substituted phosphines 26 and 27 are also shown for comparison purposes.[2a, 2c] These values support the notion that pyridinium substituents are more effective electron withdrawing groups than di(alkylamino)cyclopropenium rings (compare Entries 1 and 7), and also indicate that if appropriately substituted, pyridiniophosphines can reach donor abilities characteristic of dicationic ligands (Entries 3, 6 and 8).

In view of this analysis, the inventors tested the potential of pyridiniophosphines in catalysis and prepared a set of Pt(II) and Au(I) complexes in which salts 12-19 were used as ligands (Scheme 3). Thus, compounds 28-34 were obtained as air stable solids by addition of K$_2$PtCl$_4$ or (Me$_2$S)AuCl to solutions of the corresponding ligands. Moreover, crystals of 28 and 31 were obtained and their structure determined confirming the expected connectivity.

To compare the catalytic performance of complexes 28 and 29 with standard Pt catalysts, the hydroarylation of propargyl aryl ether 35 to chromene 36 was chosen as first model reaction because the proposed mechanism for this transformation suggests that a platinum catalyst with enhanced cationic character should facilitate the whole process. In fact, moderate accelerations were observed when (C$_6$F$_5$)$_3$P was employed as ancillary ligand or if higher oxidized Pt species such as PtCl$_4$ were used as catalysts. FIG. 3 also shows the conversion versus time plot for precatalysts 28 and 29 under otherwise identical conditions (2 mol % Pt, 80° C.). Their vastly superior performances, that clearly surpass the other catalytic mixtures, beautifully demonstrate the exquisite ability of pyridiniophosphine ligands to increase the π-acidity of Pt centres. Moreover, a qualitative correlation between the reactivity depicted by catalysts 28 and 29 and the measured oxidation potentials E$_p$ (ox) for their corresponding free ligands could be established. This additionally supports the use of cyclic voltammetry as an adequate technique to characterize the electronic properties of P-based ligands.

Importantly, other synthetically useful and mechanistically more complex Pt(II)-promoted transformations also responded to the strong π-acceptor properties of ligands 12-19. Specifically, the cycloisomerization of enyne 37 to cyclobutene 38 was chosen as additional model because this process is known to be accelerated when performed under CO atmosphere (1 atm). Hence, the study of this reaction allows a direct comparison between pyridiniophosphines and the archetypical π-acceptor ligand. FIG. 4 shows the kinetic profiles compiled for a set of different catalytic systems under otherwise identical conditions (2 mol % Pt, r.t.). As can be appreciated, CO performed better in terms of reactivity than any the other π-acceptor ligands tested, (PhO)$_3$P or (C$_6$F$_5$)$_3$P; however, the activity exhibited by catalysts 28 and 29 has no rival, and cyclobutene 38 could be obtained in excellent yields after only few minutes.

Finally, the Au-catalysed hydroarylation of phenylacetylene (39) with mesitylene (40) served as a probe of the utility of pyridiniophosphines beyond Pt chemistry. The increased π-acceptor properties of ligands 12-19 render the Au atoms in complexes 30-34 more electrophilic and as result, they should very efficiently activate alkyne 39 towards the intermolecular attack of 40. In accordance with this understanding, the results shown in FIG. 4 indicate that the catalytic activities of complexes 33 and 34 strikingly surpass that of Au catalysts based on classical π-acceptor ligands.

BRIEF DESCRIPTION OF THE DRAWINGS

The invention is further illustrated by the attached Figures. These Figures show:

In more detail, the Figures and Schemes show:

FIG. 1 illustrates structural features of the inventive pyridinium-substituted phosphines and their impact on the donor properties of the resulting ligand.

FIG. 2 depicts the structure of 12 in the solid state. The P1-C1 distance (1.8551(7) Å) is only slightly longer than the other two C—P bonds (P1-C7, 1.8260(7) Å; P1-C13, 1.8244(7) Å) probably due to the increased steric hindrance of the N-methylpyridinium rest when compared with the two phenyl rings. In addition, the degree of pyramidalization at phosphorus (61.3%) is even slightly higher than that observed for PPh₃ (56.7%). These parameters suggest retention of the nonbonding electron pair at the phosphorus atom.

FIG. 3 shows the ligand effect on the Pt-catalyzed hydroarylation of propargyl aryl ether to chromene 36.

Reagent and Conditions:
a) 33 (0.05 M), Pt precatalysts 2 mol %, AgSbF₆ 2 mol %, (CH₂)₂Cl₂, 80° C. Conversions determined by gas chromatography.

Figure 1:
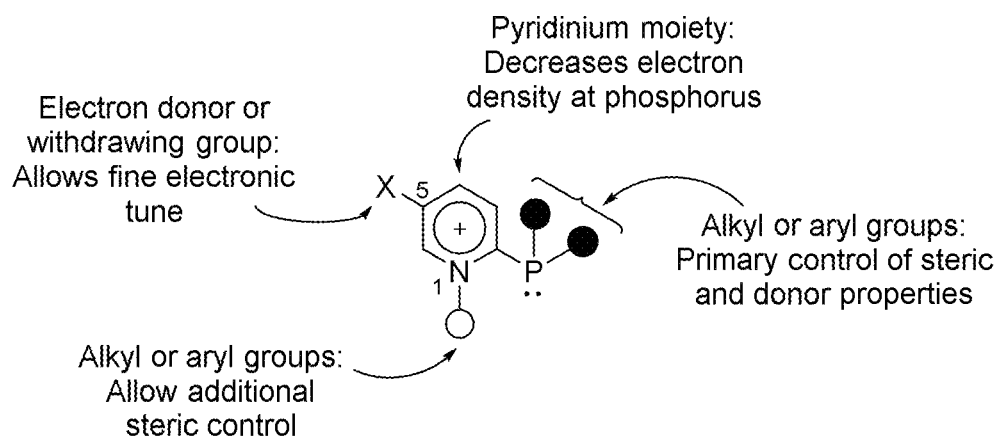
FIG. 1: Structural features of pyridinium-substituted phosphines.
Figure 2:
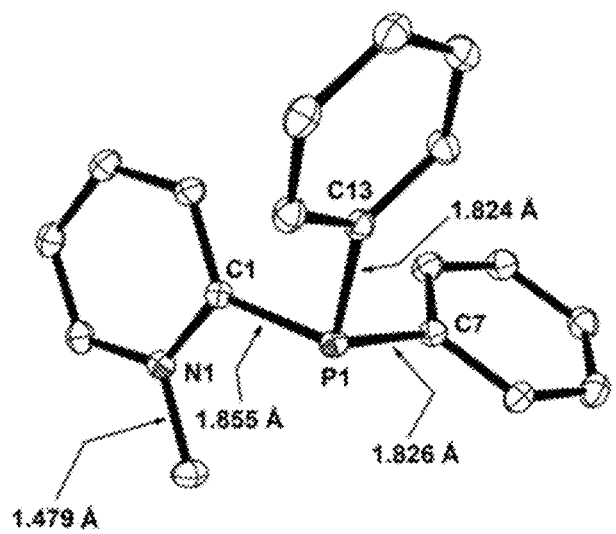
FIG. 2: Crystal structure of compound 12. Hydrogen atoms and the BF₄ anion were omitted for clarity; ellipsoids are set at 50% probability.
Figure 3:
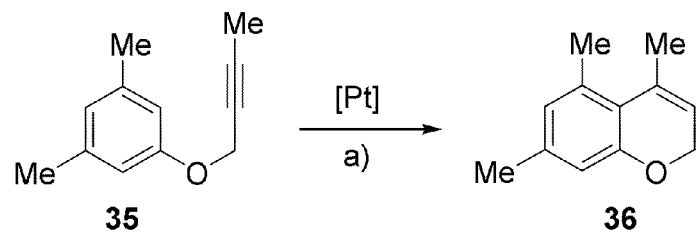
FIG. 3: Ligand effect on the Pt-catalyzed hydroarylation of propargyl aryl ether 35 to chromene 36.
Figure 3:
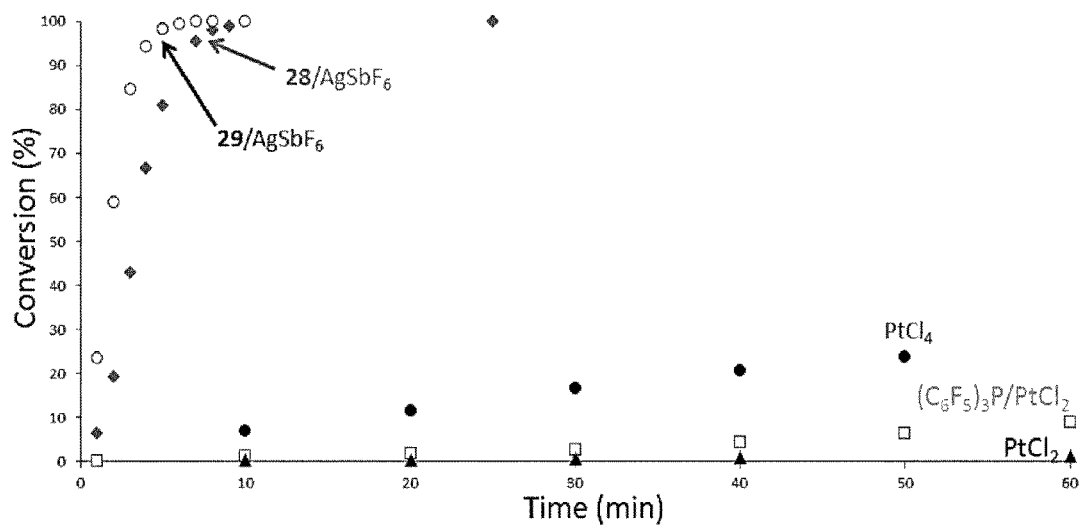
Figure 4:
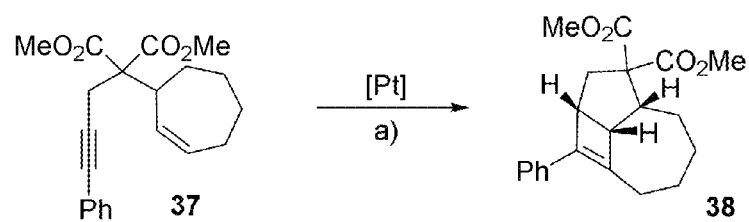
FIG. 4: Ligand effect on the Pt-catalyzed cycloisomerization of enyne 37 to cyclobutene 38.
Figure 4:
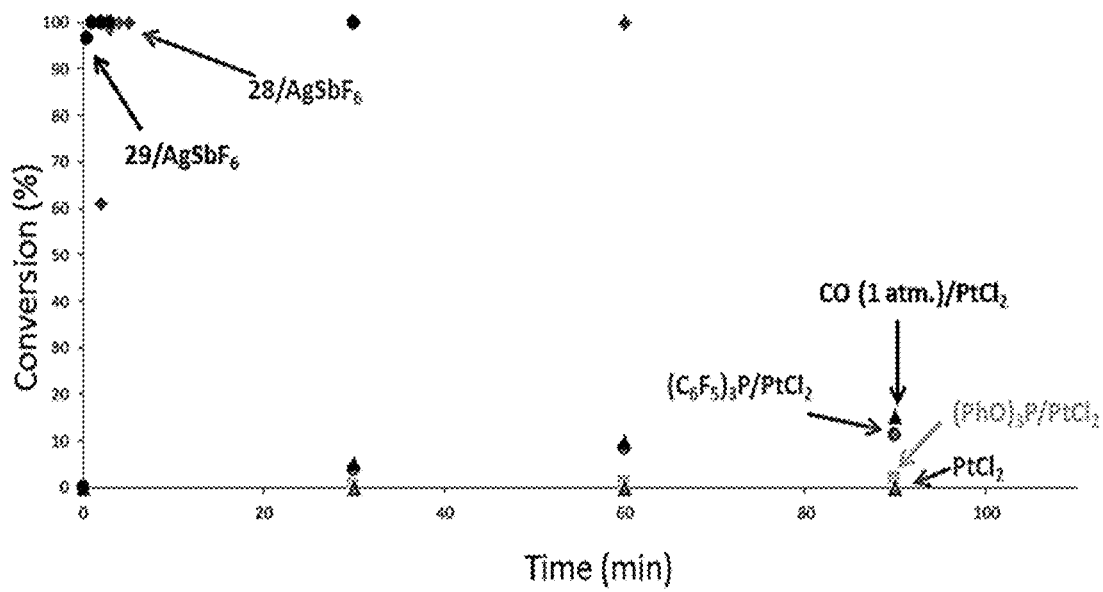

FIG. 4 shows the ligand effect on the Pt-catalyzed cycloisomerization of enyne 37 to cyclobutene 38.

Reagent and Conditions:
a) 37 (0.05 M), Pt precatalysts 2 mol %, AgSbF₆ 2 mol %, (CH₂)₂Cl₂, r.t. Conversions determined by gas chromatography.

Figure 5:
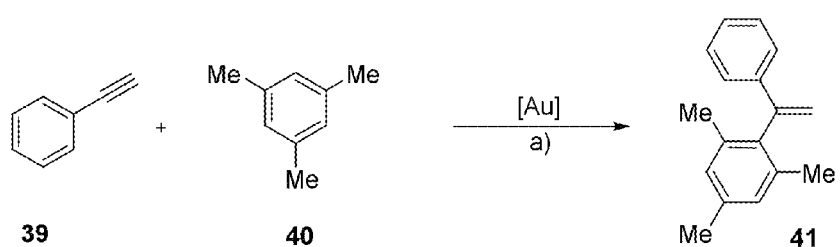
FIG. 5: Ligand effect on the Au-catalyzed hydroarylation of alkyne 39 with arene 40.
Figure 5:
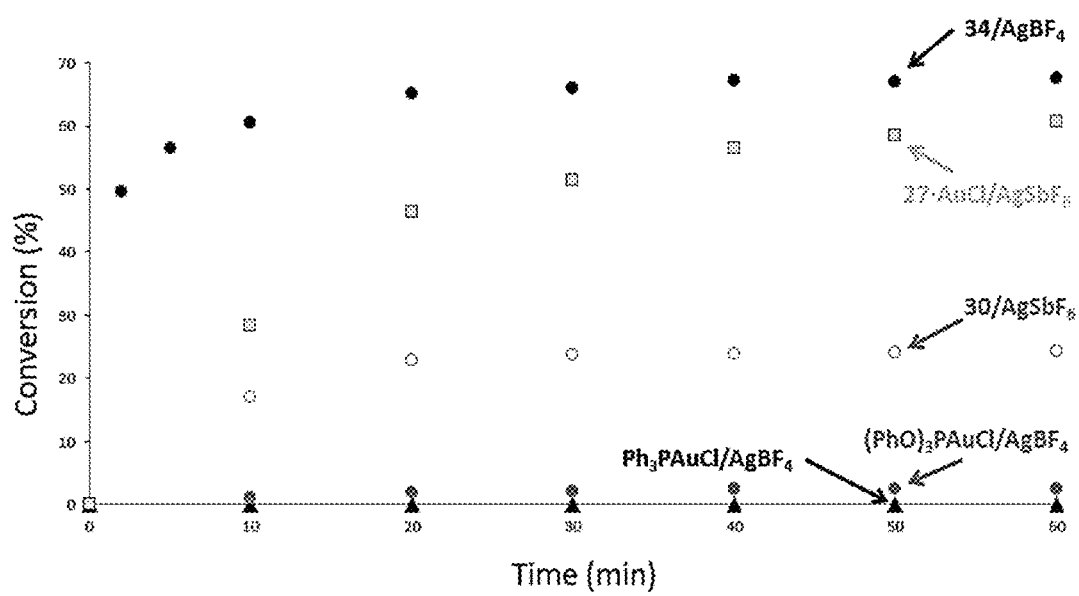

FIG. 5 shows the ligand effect on the Au-catalyzed hydroarylation of alkyne 39 with arene 40.

Reagent and Conditions:
a) 39 (0.05 M), 40 (4 equiv.; 0.2 M) Au precatalysts 5 mol %, AgX 5 mol %, (CH₂)₂Cl₂, 60° C. Conversions determined by gas chromatography.

Figure 6:
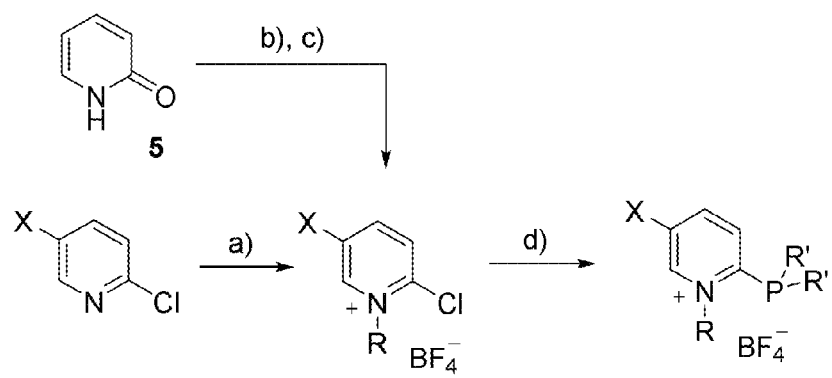
FIG. 6: Scheme 1: Synthesis of pyridinium-substituted phosphines.

FIG. 6 (Scheme 1) illustrates the synthesis of pyridinium-substituted phosphines.

Reagents and Conditions (Yields):
a) MeOBF₄ or EtOBF₄, CH₂Cl₂, rt; 6 (91%); 8 (99%); 9 (99%); 10 (98%); 11 (89%);
b) 5 (1.2 eq.), Iodobenzene (1 equiv.), CuBr (10 mol %), Cs₂CO₃ (2.1 eq), DMSO, 60° C., (95%);
c) oxalyl chloride (3 equiv.), Cl(CH₂)₂Cl, and then NaBF₄ (4 equiv.), (71%);
d) diaryl/alkylphosphine (2 equiv.), THF, 65° C.; 12 (70%), 1-3 days; 13 (80%); 14 (71%); (43%); 16 (60%); 17 (77%); 18 (89%); 19 (30%).

Figure 7:
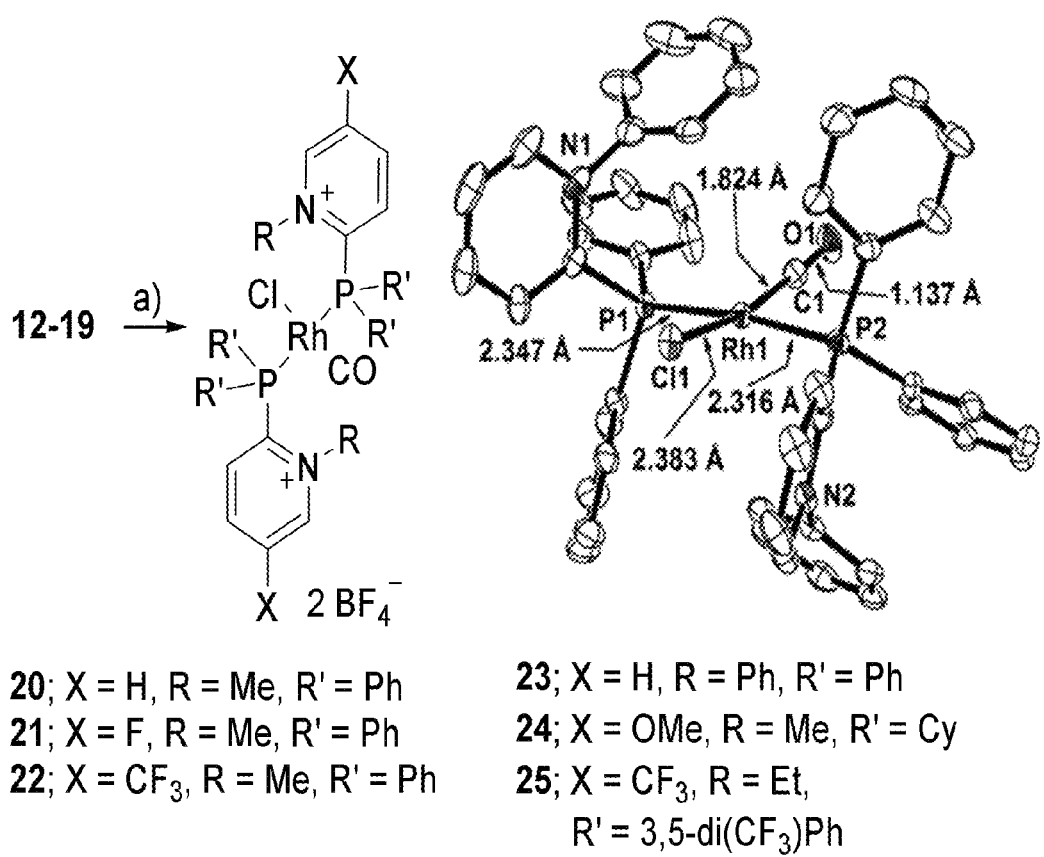
FIG. 7: Scheme 2: Synthesis of Rh complexes and crystal structure of 23. Hydrogen atoms and BF₄ anions were omitted for clarity; ellipsoids are set at 50% probability.

FIG. 7 (Scheme 2) illustrates the synthesis of Rh complexes and crystal structure of 23. Hydrogen atoms and BF₄ anions were omitted for clarity; ellipsoids are set at 50% probability.

Reagent and Conditions (Yields):
a) [RhCl(CO)₂]₂ (0.25 eq.), CH₂Cl₂, rt; 20 (99%); 21 (77%); 22 (57%); 23 (78%); 24 (74%).

Figure 8:
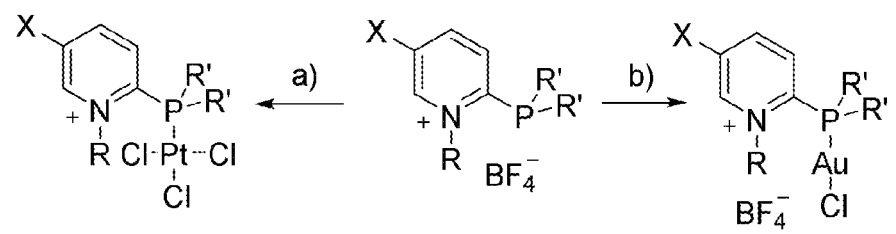
FIG. 8: Scheme 3: Synthesis of Pt and Au complexes and crystal structure of 28 and 31.
Figure 8:
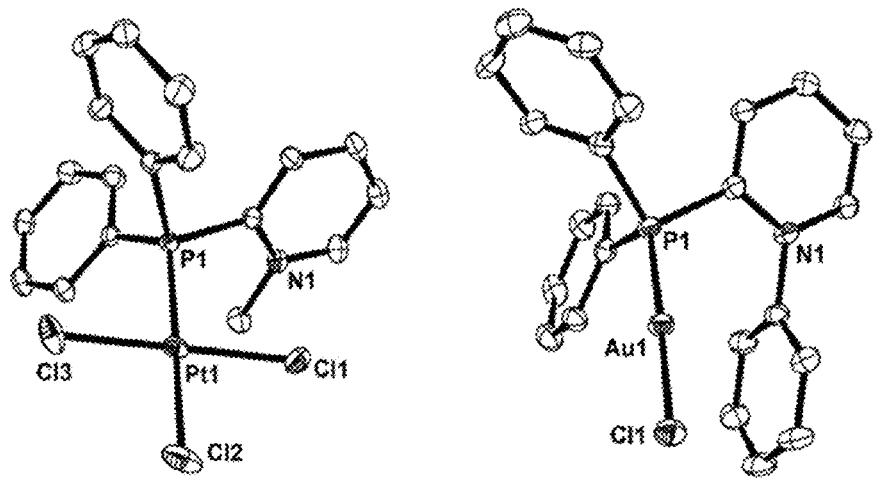

FIG. 8 (Scheme 3) illustrates the synthesis of Pt and Au complexes and crystal structure of 28 and 31. Hydrogen atoms, solvent molecules and BF₄ anions were omitted for clarity; ellipsoids are set at 50% probability.

Reagent and Conditions (Yields):
a) K₂PtCl₄ (1.0 eq.), CH₃CN, rt; 28 (80%); 29 (40%);
b) (Me₂S)AuCl (1.0 eq.), CH₂Cl₂, rt; 30 (97%); 31 (69%); 32 (98%); 33 (98%); 34 (38%).

The invention is further illustrated in the following experimental part.

General Procedures

All reactions were carried out in flame-dried glassware under Argon. All the solvents were purified by distillation over the drying agents indicated and were transferred under Argon. CH₂Cl₂ (CaH₂), hexane, toluene (Na/K). Flash chromatography: Merck silica gel 60 (230-400 mesh). IR: Nicolet FT-7199 spectrometer, wavenumbers in cm⁻¹. MS (EI): Finnigan MAT 8200 (70 eV), ESI-MS: Finnigan MAT 95, accurate mass determinations: Bruker APEX III FT-MS (7 T magnet). NMR: Spectra were recorded on a Bruker DPX 300 or AV 400 spectrometer in the solvents indicated; $^1$H and $^{13}$C chemical shifts (δ) are given in ppm relative to TMS, coupling constants (J) in Hz. The solvent signals were used as references and the chemical shifts converted to the TMS scale. All commercially available compounds (Acros, Fluka, Lancaster, Alfa Aesar, Aldrich) were used as received unless stated otherwise. Compounds 7, 35 and 37 were prepared accordingly to the procedure described in the literature.

General Procedure for the Alkylation of 2-Chloropyridines

A solution of the corresponding 2-chloropyridine (1 equiv.) in DCM (0.05 M) was added to solid Me₃OBF₄ or Et₃OBF₄ (1 equiv.) and the suspension stirred overnight. Then, the solvent was filtered off and the remaining white solid washed twice with dichloromethane and dried in vacuum.

Compound 6

Prepared from 2-chloropyridine (2.0 g, 17.6 mmol) and Me₃OBF₄ (2.6 g, 17.6 mmol) following the general procedure. After washing with DCM (2×20 ml), 6 was obtained as a white solid (3.47 g, 91%).

$^1$H NMR (300 MHz, CD₃CN) δ=8.75 (d, J=6.2 Hz, 1H), 8.47 (td, J=8.2, 1.5 Hz, 1H), 8.12 (d, J=8.3 Hz, 1H), 7.94 (t, $^3$J=6.8 Hz, 1H), 4.30 (s, 3H); $^{13}$C NMR (75 MHz, CD₃CN) δ=148.98, 148.96, 148.38, 131.00, 127.40, 48.62; IR (neat) $\tilde{v}$=712, 735, 778, 805, 1024, 1123, 1177, 1274, 1286, 1314, 1446, 1499, 1574, 1623, 3059, 3094, 3115, 3138 cm⁻¹ HRMS calcd. for C₁₂H₁₄BCl₂F₄N₂: 343.056684. found: 343.056646.

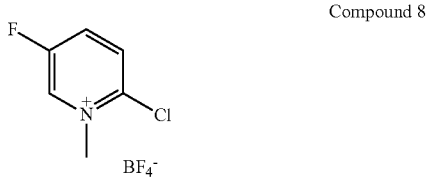

Compound 8

Prepared from 2-chloro-5-fluoropyridine (1.0 g, 7.6 mmol) and Me$_3$OBF$_4$ (1.12 g, 7.6 mmol) following the general procedure. After washing with DCM (2×20 ml), 8 was obtained as a white solid (1.75 g, 99%).

$^1$H NMR (300 MHz, CD$_3$CN) δ=8.88 (t, J=3.1 Hz, 1H), 8.36 (ddd, J=9.4, 6.7, 2.9 Hz, 1H), 8.16 (dd, J=9.3, 4.9 Hz, 1H), 4.31 (s, 3H); $^{13}$C NMR (75 MHz, CD$_3$CN) δ=159.92 (d, J$_{C-F}$=255.1 Hz), 145.62, 138.70 (d, J$_{C-F}$=40.0 Hz), 136.23 (d, J$_{C-F}$=19.8 Hz), 132.21 (d, J$_{C-F}$=7.9 Hz), 49.46; $^{19}$F NMR (282 MHz, CD$_3$CN) δ=−120.22, −151.77, −151.82; IR (neat) ṽ=655, 698, 743, 767, 854, 901, 1022, 1126, 1165, 1282, 1392, 1439, 1509, 1593, 1641, 3084, 3104 cm$^{-1}$; HRMS calcd. for C$_{12}$H$_{12}$N$_2$BCl$_2$F$_6$: 379.036928. found: 379.037035.

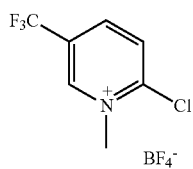

Compound 9

Prepared from 2-chloro-5-(trifluoromethyl)pyridine (400 mg, 2.2 mmol) and Me$_3$OBF$_4$ (325 mg, 2.2 mmol) following the general procedure. After washing with DCM (2×2 ml), 9 was obtained as a white solid (620 mg, 99%).

$^1$H NMR (300 MHz, CD$_3$CN) δ=9.23 (s, 1H), 8.75 (dd, J=8.7, 2.0 Hz, 1H), 8.34 (d, J=8.7 Hz, 1H), 4.39 (s, 3H); $^{13}$C NMR (75 MHz, CD$_3$CN) δ=153.30, 147.41 (m), 144.96 (q, J$_{C-F}$=3.0 Hz), 132.13, 129.37 (q, J$_{C-F}$=37.0 Hz), 122.32 (q, J$_{C-F}$=272.7 Hz), 49.45; $^{19}$F NMR (282 MHz, CD$_3$CN) δ=−63.45, −151.99, −152.04; IR (neat) ṽ=663, 690, 722, 804, 861, 888, 916, 944, 998, 1025, 1125, 1192, 1268, 1331, 1435, 1479, 1590, 1639, 2296, 2342, 2383, 3055 cm$^{-1}$; HRMS calcd. for C$_7$H$_6$NClF$_3$: 196.013540. found: 196.013563.

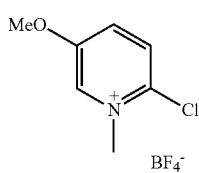

Compound 11

Prepared from 2-chloro-5-methoxypyridine (965 mg, 6.72 mmol) and Me$_3$OBF$_4$ (994 mg, 6.72 mmol) in DCM (20 ml) following the general procedure. After washing with DCM (2×20 ml), 11 was obtained as a white solid (1.47 g, 89%).

$^1$H NMR (300 MHz, CD$_3$CN) δ=8.47 (d, J=2.7 Hz, 1H), 8.10-7.93 (m, 2H), 4.27 (s, 3H), 4.00 (s, 3H); $^{13}$C NMR (75 MHz, CD$_3$CN) δ=158.33, 140.00, 136.02, 134.07, 130.94, 58.76, 48.98; $^{19}$F NMR (282 MHz, CD$_3$CN) δ=−151.67, −151.72; IR (neat) ṽ=697, 739, 847, 875, 936, 1013, 1037, 1099, 1159, 1177, 1197, 1271, 1308, 1391, 1425, 1445, 1469, 1513, 1590, 1622, 3101, 3156 cm$^{-1}$; HRMS calcd. for C$_{14}$H$_{18}$N$_2$BCl$_2$F$_4$O$_2$: 403.077864. found: 403.078070.

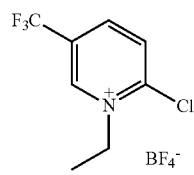

Compound 10

Prepared from 2-chloro-5-(trifluoromethyl)pyridine (1 g, 5.5 mmol) and Et$_3$OBF$_4$ (1.05 g, 5.5 mmol) in DCM (20 ml) following the general procedure and purified by filtration and washing with DCM (2×10 ml) to afford 10 as a white solid (1.6 g, 5.4 mmol, 99%).

$^1$H NMR (300 MHz, CD$_3$CN) δ=9.24 (d, J=0.7 Hz, 1H), 8.74 (dd, J=8.7, 2.1 Hz, 1H), 8.34 (d, J=8.7 Hz, 1H), 4.82 (q, J=7.3 Hz, 2H), 1.62 (t, J=7.3 Hz, 3H); $^{13}$C NMR (75 MHz, CD$_3$CN)=152.27, 146.25, 144.89 (q, J$_{C-F}$=3.0 Hz), 132.79, 129.92 (q, J$_{C-F}$=36.9 Hz), 122.21 (q, J$_{C-F}$=273.7 Hz); $^{19}$F NMR (282 MHz, CD$_3$CN) δ=−63.46, −151.88, −151.94; IR (neat) ṽ=727, 740, 767, 809, 858, 939, 1023, 1056, 1095, 1110, 1146, 1183, 1193, 1233, 1299, 1328, 1395, 1413, 1453, 1473, 1509, 1586, 1639, 3089 cm$^{-1}$; HRMS calcd. for C$_8$H$_8$NClF$_3$: 210.029185. found: 210.028857.

General Procedure for the Preparation of Pyridiniophosphines

To a solution of the corresponding 1-alkyl/aryl-2-chloropyridinium tetrafluoroborate (1 equiv.) in THF (2 ml) was added the desired secondary phosphine (2.5-3.0 equiv.) and the resulting suspension heated for 1 to 7 days. After cooling to rt, the solvents were evaporated and the crude reaction mixture washed with n-Pentan (2×2 ml), solved in DCM and washed with sat. NaBF$_4$ aqueous solution. The organic phase was dried over NaSO$_4$ and the solvent evaporated. If necessary, the resulting solid could be further purified by an additional wash with THF (1-2 ml).

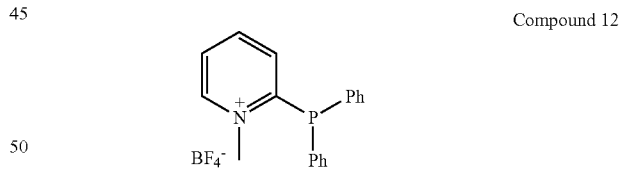

Compound 12

Prepared by heating a THF suspension of 6 (400 mg, 1.8 mmol) and diphenylphosphine (1.1 ml, 5.6 mmol) at 65° C. for 3 days. White solid (477 mg, 70%).

$^1$H NMR (300 MHz, CDCl$_3$) δ=9.04 (d, J=5.7 Hz, 1H), 8.25 (td, J=7.9, 0.9 Hz, 1H), 8.03-7.95 (m, 1H), 7.57-7.43 (m, 6H), 7.39-7.27 (m, 5H), 4.30 (d, J=1.1 Hz, 3H); $^{13}$C NMR (75 MHz, CDCl$_3$) δ=161.02 (d, J$_{C-P}$=33.4 Hz), 149.54, 144.04, 134.70 (d, J$_{C-P}$=21.7 Hz), 132.63, 131.60, 130.20 (d, J$_{C-P}$=8.4 Hz), 129.03 (d, J=6.7 Hz), 127.96, 47.64 (d, J$_{C-P}$=21.0 Hz); $^{31}$P NMR (121 MHz, CDCl$_3$) δ=−8.61; IR (neat) ṽ=696, 724, 748, 798, 954, 1000, 1038, 1051, 1161, 1181, 1265, 1310, 1436, 1492, 1571, 1610, 3055, 3103, 3134 cm$^{-1}$; HRMS calcd. for C$_{18}$H$_{17}$NP: 278.109315. found: 278.109239.

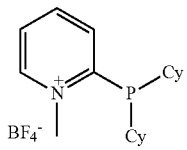

Compound 13

Prepared by heating a THF suspension of 6 (500 mg, 2.3 mmol) and dicyclohexylphosphine (0.75 ml, 5.8 mmol) at 65° C. for 3 days. White solid (699 mg, 80%).

$^1$H NMR (400 MHz, CDCl$_3$) δ=9.11 (d, J=5.2 Hz, 1H), 8.48 (t, J=7.8 Hz, 1H), 8.05 (dd, J=14.3, 7.5 Hz, 2H), 4.59 (s, 3H), 2.11 (t, J=11.8 Hz, 2H), 1.91 (d, J=12.0 Hz, 2H), 1.81 (d, J=12.8 Hz, 2H), 1.69 (t, J=11.9 Hz, 4H), 1.51 (d, J=12.5 Hz, 2H), 1.41-1.01 (m, 10H); $^{13}$C NMR (101 MHz, CDCl$_3$) δ=160.33 (d, J$_{C-P}$=42.5 Hz), 149.73, 143.58, 133.44 (d, J$_{C-P}$=3.2 Hz), 128.24, 48.82 (d, J$_{C-P}$=26.1 Hz), 34.36 (d, J$_{C-P}$=15.1 Hz), 29.95 (d, J$_{C-P}$=15.9 Hz), 29.44 (d, J$_{C-P}$=8.6 Hz), 26.78 (d, J$_{C-P}$=12.5 Hz), 26.65 (d, J$_{C-P}$=8.8 Hz), 25.91; $^{31}$P NMR (162 MHz, CDCl$_3$) δ=−3.52; IR (neat) ṽ=728, 779, 851, 915, 1053, 1179, 1262, 1448, 1497, 1571, 1610, 2851, 2925 cm$^1$; HRMS calcd. for C$_{18}$H$_{29}$NP: 290.203217. found: 290.203415.

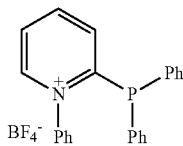

Compound 14

Prepared by heating a THF suspension of 7 (650 mg, 2.3 mmol) and diphenylphosphine (1.2 ml, 6.9 mmol) at 130° C. for 12 h in a µwave oven. White solid (715 mg, 71%).

$^1$H NMR (300 MHz, CDCl$_3$) δ=8.76 (d, J=5.1 Hz, 1H), 8.46 (td, J=8.0 Hz, 1.3, 1H), 8.06 (t, J=6.9 Hz, 1H), 7.66-7.50 (m, 4H), 7.50-7.37 (m, 6H), 7.32-7.21 (m, 6H); $^{13}$C NMR (75 MHz, CD$_3$CN) δ=149.53, 146.74, 135.83 (d, J$_{C-P}$=22.5 Hz), 134.40, 132.53, 132.11, 131.40 (d, J$_{C-P}$=8.2 Hz), 130.58 (d, J$_{C-P}$=7.6 Hz), 128.25, 127.40 (d, J$_{C-P}$=3.8 Hz); $^{19}$F NMR (282 MHz, CDCl$_3$) δ=−151.82, −151.87; $^{31}$P NMR (121 MHz, CDCN) δ=−7.74; IR (neat) ṽ=692, 699, 734, 748, 757, 786, 841, 863, 901, 931, 979, 997, 1011, 1035, 1047, 1079, 1163, 1178, 1254, 1288, 1315, 1438, 1455, 1475, 1492, 1563, 1589, 1607, 3070, 3117 cm$^{-1}$; HRMS calcd. for C$_{23}$H$_{19}$NP: 340.124626. found: 360.124961.

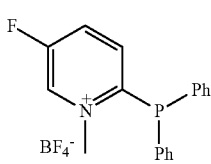

Compound 15

Prepared by heating a THF suspension of 8 (500 mg, 2.14 mmol) and diphenylphosphine (0.92 ml, 5.35 mmol) at 65° C. for 3 days. White solid (351 mg, 43%).

$^1$H NMR (300 MHz, CD$_3$CN) δ=8.94-8.82 (m, 1H), 8.18-8.07 (m, 1H), 7.58 (m, 6H), 7.42 (m, 5H), 4.23 (d, J=1.4 Hz, 3H); $^{13}$C NMR (75 MHz, CDCN) δ=160.91 (d, J$_{C-F}$=255.7 Hz), 139.81 (d, J$_{C-P}$=38.2 Hz), 135.66 (d, J$_{C-P}$=0.9 Hz), 135.62 (d, J$_{C-P}$=21.9 Hz), 132.84 (d, J$_{C-P}$=17.4 Hz), 132.43 (d, J$_{C-P}$=0.6 Hz), 130.92 (d, J$_{C-P}$=8.3 Hz), 130.28 (d, J$_{C-P}$=6.7 Hz), 49.12 (d, J$_{C-P}$=21.5 Hz); $^{31}$P NMR (121 MHz, CDCl$_3$) δ=−9.34; IR (neat) ṽ=699, 715, 738, 753, 760, 858, 895, 931, 958, 998, 1024, 1143, 1165, 1181, 1273, 1314, 1384, 1436, 1479, 1500, 1583, 1623 cm$^{-1}$; HRMS calcd. for C$_{18}$H$_{16}$NFP: 296.099965. found: 296.099889.

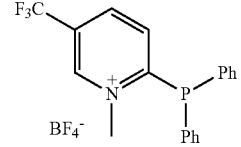

Compound 16

Prepared by heating a THF suspension of 9 (500 mg, 1.8 mmol) and diphenylphosphine (0.62 ml, 4.4 mmol) at 65° C. for 1 day. White solid (451 mg, 60%).

$^1$H NMR (300 MHz, CD$_3$CN) δ=9.18 (s, 1H), 8.51 (dd, J=8.4, 1.3 Hz, 1H), 7.72-7.50 (m, 7H), 7.50-7.38 (m, 4H), 4.25 (d, J=1.0 Hz, 3H); $^{13}$C NMR (75 MHz, CD$_3$CN) δ=167.44 (d, J$_{C-P}$=35.6 Hz), 147.74, 141.70 (q, J$_{C-F}$=3.0 Hz), 135.92 (d, J$_{C-P}$=22.0 Hz), 134.82 (d, J$_{C-P}$=1.2 Hz), 132.72, 131.05 (d, J$_{C-P}$=8.6 Hz), 129.85 (q, J$_{C-F}$=36.1), 129.43 (d, J$_{C-P}$=6.0 Hz), 122.51 (q, J$_{C-F}$=272.6 Hz), 49.24 (d, J$_{C-P}$=20.7); $^{19}$F NMR (282 MHz, CD$_3$CN) δ=−63.67, −151.79, −151.84; $^{31}$P NMR (121 MHz, CD$_3$CN) δ=−6.00; IR (neat) ṽ=693, 702, 727, 743, 752, 862, 892, 913, 996, 1048, 1090, 1115, 1148, 1174, 1267, 1342, 1435, 1504, 1579, 1639, 3103 cm$^{-1}$; HRMS calcd. for C$_{19}$H$_{16}$NF$_3$P: 346.09727. found: 346.097027.

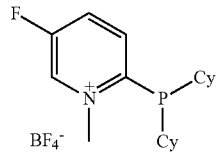

Compound 17

Prepared by heating a THF suspension of 8 (500 mg, 2.14 mmol) and dicyclohexylphosphine (1.08 ml, 5.35 mmol) at 65° C. during 12 hours. White solid (648 mg, 77%).

$^1$H NMR (300 MHz, CDCl$_3$) δ=9.06 (d, J=2.3 Hz, 1H), 8.34-8.21 (m, 1H), 8.21-8.08 (m, 1H), 4.64 (s, 3H), 2.12 (t, J=11.5 Hz, 2H), 1.98-1.61 (m, 8H), 1.52 (d, J=11.7 Hz, 2H), 1.44-1.02 (m, 10H); $^{13}$C NMR (75 MHz, CD$_3$CN) δ=160.88 (d, J$_{C-F}$=255.9 Hz), 158.18 (dd, J$_{C-P}$=43.7, J$_{C-F}$=4.2 Hz), 140.06 (d, J$_{C-P}$=36.1 Hz), 136.29 (dd, J$_{C-P}$=7.4 Hz, J$_{C-F}$=3.4 Hz), 131.93 (d, J$_{C-P}$=17.2 Hz), 50.13 (d, J$_{C-P}$=26.4 Hz), 34.72 (d, J$_{C-P}$=14.3 Hz), 30.48 (d, J$_{C-P}$=16.2 Hz), 30.01 (d, J$_{C-P}$=8.7 Hz), 27.42 (d, J$_{C-P}$=10.9 Hz), 27.28 (d, J$_{C-P}$=10.9 Hz), 26.61; $^{19}$F NMR (282 MHz, CDCl$_3$) δ=−118.61, −151.62, −151.67; $^{31}$P NMR (121 MHz, CD$_3$CN) δ=−4.49; IR (neat) ṽ=704, 738, 765, 817, 851, 889, 920, 958, 1004, 1025, 1040, 1057, 1112, 1170, 1182, 1202, 1269, 1279, 1433, 1450, 1504, 1582, 1626, 2852, 2925, 3077 cm$^{-1}$; HRMS calcd. for C$_{18}$H$_{17}$NP: 308.193442. found: 308.193793.

Compound 18

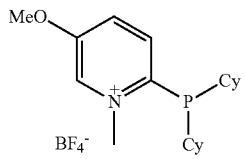

Prepared by heating a THF suspension off 11 (500 mg, 2.05 mmol) and dicyclohexylphosphin (1.25 ml, 6.16 mmol) at 65° C. during 12 hours. White solid (744 mg, 89%).

$^1$H NMR (300 MHz, CDCl$_3$) δ=8.48 (d, J=2.1 Hz, 1H), 8.04 (d, J=9.0 Hz, 1H), 7.94 (dd, J=9.0, 2.6 Hz, 1H), 4.43 (s, 3H), 4.01 (s, 3H), 2.21-2.08 (m, 2H), 1.85-0.96 (m, 20H); $^{13}$C NMR (75 MHz, CD$_3$CN) δ=159.15, 138.13, 135.35, 135.31, 58.35, 49.85 (d, J$_{C-P}$=27.5 Hz), 34.82 (d, J$_{C-P}$=13.5 Hz), 30.76 (d, J$_{C-P}$=16.9 HZ), 29.97 (d, J$_{C-P}$=8.1 Hz), 27.48 (d, J=13.2 Hz), 27.34 (d, J$_{C-P}$=8.8 Hz), 26.73 (d, J$_{C-P}$=1.1 Hz); $^{19}$F NMR (282 MHz, CDCl$_3$) δ=−151.83, −151.88; $^{31}$P NMR (121 MHz, CDCN) δ=−7.27; IR (neat) ṽ=704, 741, 816, 842, 884, 916, 1000, 1015, 1035, 1046, 1163, 1187, 1196, 1286, 1317, 1434, 1447, 1507, 1574, 1615, 2845, 2920 cm$^{-1}$; HRMS calcd. for C$_{19}$H$_{31}$NOP: 320.213778. found: 320.213335.

Compound 19

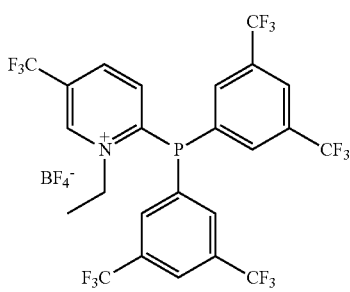

To a suspension of KH (8.75 mg, 0.22 mmol) in THF (2 ml) was added bis(3,5-bis(trifluoromethyl)phenyl) phosphine (100 mg, 0.22 mmol) at −78° C. and the resulting deep red suspension stirred for 1 hour. Then, the suspension was transferred at the same temperature to a precooled suspension (−78° C.) of 10 (64.9 mg, 0.22 mmol) in THF (2 ml) and the mixture allowed to warm up to rt and stirred for 3 days. After evaporation of the solvent and washing with DCM (2×2 ml), compound 19 was obtained as an off white solid (48 mg, 30%).

$^1$H NMR (300 MHz, CDCl$_3$) δ=9.32 (s, 1H), 8.62 (d, J=7.7 Hz, 1H), 8.25 (s, 2H), 8.02 (d, J=7.2 Hz, 4H), 7.92 (d, J=7.9 Hz, 1H), 4.88 (m, 2H), 1.56 (t, J=7.3 Hz, 3H); $^{13}$C NMR (75 MHz, CD$_3$CN) δ=161.99 (d, J$_{C-P}$=33.4 Hz), 147.95-146.40 (m), 143.99-142.39 (m), 137.44, 136.89-136.01 (m), 133.59 (qd, J$_{C-F}$=33.9 Hz, J$_{C-P}$=7.7 Hz), 133.19 (d, J$_{C-P}$=13.5 Hz), 132.18 (d, J$_{C-F}$=36.9 Hz), 124.10 (q, J$_{C-F}$=272.4 Hz), 121.46 (q, J$_{C-F}$=273.0 Hz), 58.60 (d, J$_{C-P}$=23.4 Hz), 16.29 (d, J$_{C-F}$=3.5 Hz); $^{19}$F NMR (282 MHz, CDCl$_3$) δ=−63.52, −63, 68, −151.80, −151.85; $^{31}$P NMR (121 MHz, CDCN) δ=−10.52; IR (neat) ṽ=682, 700, 741, 767, 846, 862, 900, 913, 1051, 1095, 1120, 1279, 1331, 1356, 1405, 1459, 1502, 1588, 1634, 2001, 3090 cm$^{-1}$; HRMS calcd. for C$_{24}$H$_{14}$F$_{15}$NP: 632.062949. found: 632.061889.

General Procedure for the Preparation of Pyridiniophosphine Rhodium Complexes

[Rh(CO)$_2$Cl]$_2$ (0.25 equiv.) was added to a solution of the corresponding pyridiniophosphine ligand (1 equiv.) in DCM (2 ml). The resulting suspension was stirred for 1 hour at rt and after evaporation of the solvent, the solid was washed with n-pentan (2×2 ml) and dried in vacuum. These compounds can be crystallized from acetonitrile/ether mixtures.

Compound 20

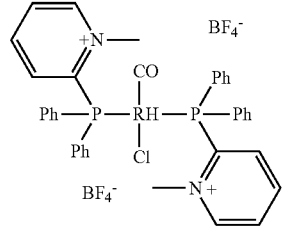

Prepared from 12 (100 mg, 0.274 mmol) and [Rh(CO)Cl$_2$]$_2$ (26.6 mg, 0.063 mmol) following the general procedure. Yellow solid (121 mg, 99%).

$^1$H NMR (300 MHz, CDCN) δ=8.84 (d, J=5.9 Hz, 2H), 8.38 (t, J=7.7 Hz, 2H), 8.11-8.02 (m, 2H), 7.84 (s, 8H), 7.79-7.72 (m, 4H), 7.72-7.58 (m, 10H), 4.50 (s, 6H); $^{13}$C NMR (75 MHz, CDCN) δ=186.07 (dt, J$_{C-Rh}$=31.9 Hz, J$_{C-P}$=15.6 Hz), 153.59 (t, J$_{C-P}$=18.1 Hz), 151.14, 145.60, 136.20, 134.99, 134.20, 131.14, 130.07, 126.58 (t, J$_{C-P}$=24.3 Hz), 50.82; $^{31}$P NMR (121 MHz, CDCN) δ=37.82 (d, J$_{P-Rh}$=130.7 Hz); IR (neat) ṽ=692, 707, 752, 773, 799, 900, 931, 998, 1056, 1165, 1182, 1274, 1314, 1411, 1438, 1481, 1499, 1576, 1610, 1996, 3093, 3138 cm$^{-1}$; HRMS calcd. for C$_{37}$H$_{34}$BClF$_4$N$_2$OP$_2$Rh: 809.092884. found: 809.093025.

Compound 21

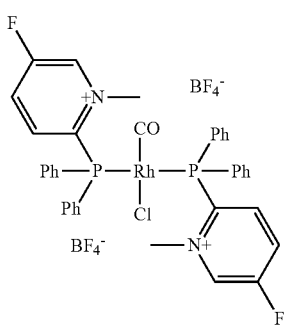

Prepared from 15 (75 mg, 0.2 mmol) and [Rh(CO)$_2$Cl]$_2$ (19.3 mg, 0.05 mmol) following the general procedure. Yellow solid (121 mg, 69%).

$^1$H NMR (300 MHz, CDCN) δ=8.98 (s, 2H), 8.27-8.16 (m, 2H), 7.84 (s, 8H), 7.76 (t, J=7.4 Hz, 4H), 7.68 (t, J=7.6 Hz, 10H), 4.54 (s, 6H); $^{13}$C NMR (75 MHz, CDCN) δ=161.59 (d, J$_{C-F}$=259.3 Hz), 150.65, 141.69 (d, J$_{C-F}$=38.2 Hz), 136.72 (d, J$_{C-P}$=8.5 Hz), 136.17, 134.35, 132.75 (d, J$_{C-F}$=17.3 Hz), 131.22, 126.48, 51.51 (d, J$_{C-P}$=1.6 Hz); $^{31}$P NMR (121 MHz, CDCN) δ=39.02 (d, J$_{Rh-P}$=130.7 Hz); IR (neat) ṽ=694, 738, 754, 850, 962, 998, 1054, 1169, 1282, 1437, 1482, 1505, 1590, 1624, 1994, 3087 cm$^{-1}$; HRMS calcd. for C$_{37}$H$_{32}$BClF$_6$N$_2$OP$_2$Rh: 845.074040. found: 845.073864.

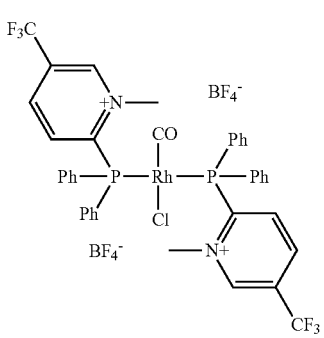

Compound 22

Prepared from 16 (100 mg, 0.231 mmol) and [Rh(CO)$_2$Cl]$_2$ (22.5 mg, 0.058 mmol) following the general procedure. Yellow solid (68 mg, 57%).

$^1$H NMR (300 MHz, CDCN) δ=9.28 (s, 2H), 8.65 (d, J=8.2 Hz, 2H), 7.95-7.63 (m, 22H), 4.56 (s, 6H); $^{13}$C NMR (75 MHz, CDCN) δ=167.45 (d, J$_{C-P}$=36.8 Hz), 147.80, 141.73, 136.46 (d, J$_{C-P}$=22.1 Hz), 134.84, 132.76, 131.08 (d, J$_{C-P}$=8.5 Hz), 129.81 (d, J$_{C-P}$=36.7 Hz), 129.44 (d, J$_{C-P}$=5.4 Hz), 122.54 (q, J$_{C-F}$=272.8 Hz), 47.26 (d, J$_{C-P}$=20.6 Hz); $^{31}$P NMR (121 MHz, CDCN) δ=40.44 (d, J$_{Rh-P}$=131.0 Hz); IR (neat) $\tilde{v}$=691, 705, 752, 858, 890, 932, 998, 1052, 1090, 1118, 1159, 1177, 1243, 1275, 1334, 1392, 1438, 1482, 1509, 1586, 1634, 1741, 2004, 3092 cm$^{-1}$; HRMS calcd. for C$_{39}$H$_{32}$BClF$_{10}$N$_2$OP$_2$Rh: 945.067689. found: 945.067581.

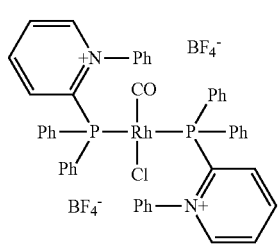

Compound 23

Prepared from 14 (100 mg, 0.253 mmol) and [Rh(CO)$_2$Cl]$_2$ (24.6 mg, 0.063 mmol) following the general procedure. Yellow solid (94 mg, 78%).

$^1$H NMR (300 MHz, CDCl$_3$) δ=8.62 (d, J=5.6 Hz, 2H), 8.49 (t, J=7.9 Hz, 2H), 8.17-8.07 (m, 4H), 7.78 (dd, J=12.7, 6.3 Hz, 8H), 7.54 (ddd, J=22.9, 14.9, 7.8 Hz, 16H), 7.33 (t, J=7.5 Hz, 2H), 6.91 (t, J=8.0 Hz, 4H); $^{13}$C NMR (101 MHz, CDCN) δ=154.96, 151.72, 146.24, 142.28, 136.52 (t, J$_{C-P}$=7.2 Hz), 136.12-135.26 (m), 133.73, 132.75, 130.74 (t, J$_{C-P}$=5.5 Hz), 130.48, 129.97, 128.15, 127.91, 127.71; $^{31}$P NMR (121 MHz, CDCl$_3$) δ=42.09 (d, J$_{Rh-P}$=134.4 Hz); IR (neat) $\tilde{v}$=692, 749, 925, 998, 1034, 1048, 1182, 1254, 1286, 1318, 1437, 1457, 1479, 1587, 1603, 1981, 2350, 3060 cm$^{-1}$; HRMS calcd. for C$_{47}$H$_{38}$BClF$_4$N$_2$OP$_2$Rh: 933.124354. found: 933.123835.

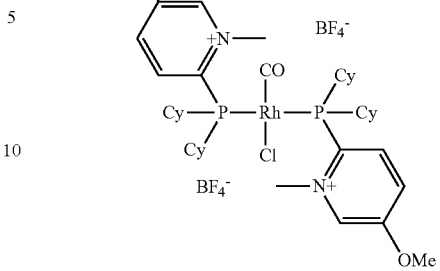

Compound 24

Prepared from 18 (75 mg, 0.184 mmol) and [Rh(CO)$_2$Cl]$_2$ (17.9 mg, 0.046 mmol) following the general procedure. Yellow solid (67 mg, 74%).

$^1$H NMR (300 MHz, DMSO) δ=9.11 (s, 2H), 8.38 (d, J=9.1 Hz, 2H), 8.20 (dd, J=9.0, 2.3 Hz, 2H), 4.90 (s, 6H), 4.08 (s, 6H), 2.17 (s, 4H), 2.02-0.94 (m, 40H); $^{13}$C NMR (101 MHz, DMSO) δ=185.13 (dt, J$_{C-Rh}$=33.4 Hz, J$_{C-P}$=16.4 Hz), 158.14, 140.35, 138.33 (t, J$_{C-P}$=12.9 Hz), 134.89, 127.44, 57.59, 51.11 (t, J$_{C-P}$=4.2 Hz), 36.04, 33.28, 29.39, 28.39, 27.61, 26.59, 25.77, 25.49; $^{31}$P NMR (121 MHz, DMSO) δ=40.26 (d, J$_{Rh-P}$=123.0 Hz); IR (neat) $\tilde{v}$=706, 739, 765, 815, 854, 888, 918, 940, 1018, 1050, 1098, 1172, 1180, 1207, 1269, 1317, 1415, 1450, 1475, 1515, 1614, 1974, 2850, 2928 cm$^{-1}$; HRMS calcd. for C$_{39}$H$_{62}$BClF$_4$N$_2$O$_3$P$_2$Rh: 893.301860. found: 893.302947.

General Procedure for the Preparation of the Phosphine Platinum Complexes

Finely grounded K$_2$PtCl$_4$ (1 equiv) was added to a solution of the pyridiniophosphine salt (1 equiv.) in MeCN (2 ml) and the resulting suspension stirred overnight at rt. After evaporation of the solvent, the solid was washed with n-Pentan (2×2 ml), crystallized from DMSO/DCM and dried in vacuum to yield the desired platinum complexes.

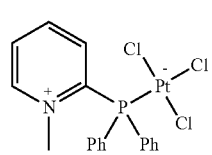

Compound 28

Prepared from 12 (100 mg, 0.274 mmol) and K$_2$PtCl$_4$ (114 mg, 0.274 mmol) following the general procedure. White solid (127 mg, 80%).

$^1$H NMR (300 MHz, DMSO) δ=9.18 (d, J=5.7 Hz, 1H), 8.53 (t, J=7.9 Hz, 1H), 8.20 (t, J=6.9 Hz, 1H), 8.02 (dd, J=12.3 Hz, J=7.2 Hz, 4H), 7.79-7.57 (m, 6H), 7.39 (t, J=7.0 Hz, 1H), 4.35 (s, 3H); $^{13}$C NMR (75 MHz, CD$_3$CN) δ=150.13, 144.54 (d, J$_{C-P}$=5.7 Hz), 135.32 (d, J$_{C-P}$=11.6 Hz), 132.81 (d, J$_{C-P}$=7.5 Hz), 132.63 (d, J$_{C-P}$=2.5 Hz), 129.28 (d, J$_{C-P}$=11.6 Hz), 128.78, 124.56, 123.71, 48.32 (d, J$_{C-P}$=7.3 Hz); $^{31}$P NMR (121 MHz, DMSO) δ=8.49 (J$_{C-Pt}$=1954 Hz); IR (neat) $\tilde{v}$=673, 822, 1003, 1023, 1051, 1659, 2126, 2253, 2342, 2383 cm$^{-1}$; HRMS for DMSO adduct calcd. for C$_{20}$H$_{23}$Cl$_2$NOPPtS: 621.024487. found: 621.024734.

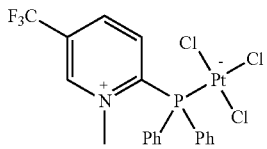

Compound 29

Prepared from 16 (100 mg, 0.231 mmol) and K$_2$PtCl$_4$ (96 mg, 0.231 mmol) following the general procedure. White solid (59 mg, 40%).

$^1$H NMR (300 MHz, DMSO) δ=9.85 (s, 1H), 8.98 (d, J=8.2 Hz, 1H), 8.05 (dd, J=12.4 Hz, J=7.4 Hz, 4H), 7.81-7.60 (m, 6H), 7.55 (dd, J=7.5 Hz, J=7.1 Hz, 1H), 4.42 (s, 3H); $^{13}$C NMR (75 MHz, CD$_3$CN) δ=155.07 (d, J$_{C-P}$=46.9 Hz), 148.54, 141.59, 135.47 (d, J$_{C-P}$=11.7 Hz), 133.48 (d, J$_{C-P}$=7.7 Hz), 132.99, 129.46 (d, J$_{C-P}$=11.6 Hz), 128.77 (d, J$_{C-P}$=36.1 Hz), 123.54 (d, J$_{C-P}$=64.0 Hz), 121.24 (q, J$_{C-P}$=273.6 Hz), 49.19 (d, J$_{C-P}$=6.8 Hz); $^{31}$P NMR (121 MHz, DMSO) δ=10.63 (J$_{C-Pt}$=1953 Hz); IR (neat) ṽ=692, 704, 725, 755, 872, 890, 1036, 1114, 1148, 1179, 1192, 1270, 1332, 1388, 1438, 1481, 1508, 1631, 3001, 3044 cm$^{-1}$; HRMS for DMSO adduct calcd. for C$_{21}$H$_{22}$Cl$_2$F$_3$NOPPtS: 689.013152. found: 689.014029.

General Procedure for the Preparation of the Phosphine Gold Complexes

AuCl.SMe$_2$ (1 equiv.) was added to a solution of the desired pyridiniophosphine salt (1 equiv.) in DCM (2 ml) and the resulting suspension stirred for 1 hour at rt. After evaporation of the solvent, the resulting solid washed with n-Pentan (2×2 ml) and dried in vacuum to yield the desired gold complexes.

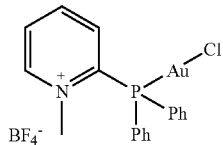

Compound 30

Prepared from 12 (100 mg, 0.274 mmol) and AuCl.SMe$_2$ (80.7 mg, 0.274 mmol) following the general procedure. White solid (159 mg, 99%).

$^1$H NMR (300 MHz, CDCl$_3$) δ=9.06 (d, J=0.5 Hz, 1H), 8.44 (t, J=7.7 Hz, 1H), 8.20 (t, J=6.4 Hz, 1H), 7.86-7.53 (m, 10H), 7.38 (t, J=7.5 Hz, 1H), 4.45 (s, 3H); $^{13}$C NMR (75 MHz, CDCl$_3$) δ=151.71, 147.12 (d, J$_{C-P}$=52.2 Hz), 145.39 (d, J=5.6 Hz), 134.83 (d, J$_{C-P}$25=15.6 Hz), 134.05 (d, J$_{C-P}$=2.0 Hz), 133.77 (d, J$_{C-P}$=9.3 Hz), 130.48 (d, J$_{C-P}$=12.8 Hz), 122.55, 121.90, 48.64 (d, J$_{C-P}$=11.4 Hz); $^{31}$P NMR (121 MHz, CDCl$_3$) δ=30.88; IR (neat) ṽ=692, 729, 913, 998, 1055, 1097, 1162, 1185, 1278, 1438, 1482, 1500, 1609, 3061, 3138 cm$^{-1}$; HRMS calcd. for C$_{18}$H$_{17}$NAuClP: 510.044722. found: 510.044585.

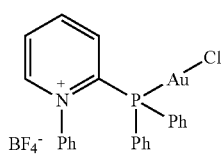

Compound 31

Prepared from 14 (50 mg, 0.12 mmol) and AuCl.SMe$_2$ (34.5 mg, 0.12 mmol) following the general procedure. White solid (53 mg, 68%).

$^1$H NMR (400 MHz, CD$_3$CN) δ=8.94 (s, 1H), 8.63 (t, J=8.0 Hz, 1H), 8.29 (t, J=6.7 Hz, 1H), 7.83-7.59 (m, 12H), 7.43 (t, J=8.0 Hz, 2H), 7.23 (d, J=7.9 Hz, 2H); $^{13}$C NMR (101 MHz, CD$_3$CN) δ=152.22, 148.28 (d, J$_{C-P}$=5.2 Hz), 141.55 (d, J$_{C-P}$=4.5 Hz), 136.26 (d, J$_{C-P}$=15.9 Hz), 136.10 (d, J$_{C-P}$=8.2 Hz), 134.89 (d, J$_{C-P}$=2.5 Hz), 133.32, 131.31 (d, J$_{C-P}$=3.2 Hz), 131.17, 131.01, 127.87, 125.84, 125.22; $^{31}$P NMR (162 MHz, CD$_3$CN) δ=31.36; IR (neat) ṽ=668, 689, 712, 735, 753, 765, 786, 853, 926, 980, 997, 1030, 1044, 1099, 1144, 1162, 1189, 1256, 1283, 1433, 1442, 1458, 1483, 1587, 1603, 3060 cm$^1$; HRMS calcd. for C$_{23}$H$_{19}$NAuClP: 572.060365. found: 572.060083.

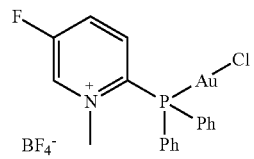

Compound 32

Prepared from 15 (100 mg, 0.26 mmol) and AuCl.SMe$_2$ (76.6 mg, 0.26 mmol) following the general procedure. White solid (166 mg, 97%).

$^1$H NMR (400 MHz, CD$_3$CN) δ=9.02 (dd, J=6.0 Hz, 2.7, 1H), 8.27 (ddd, J=9.1, 6.6, 2.6 Hz, 1H), 7.88-7.63 (m, 10H), 7.58-7.48 (m, 1H), 4.40 (s, 3H); $^{13}$C NMR (101 MHz, CD$_3$CN) δ=162.24 (d, J$_{C-F}$=260.5 Hz), 142.99 (d, J$_{C-P}$=37.3 Hz), 137.51 (dd, J$_{C-F}$=10.0 Hz, J$_{C-P}$=8.4 Hz), 136.23 (d, J$_{C-P}$=15.9 Hz), 135.36 (d, J$_{C-P}$=2.6 Hz), 133.81 (d, J$_{C-P}$=6.2 Hz), 133.58 (d, J$_{C-P}$=6.3 Hz), 131.65 (d, J$_{C-P}$=12.8 Hz), 123.98 (d, J$_{C-P}$=62.6 Hz), 50.70 (d, J$_{C-P}$=11.9 Hz); $^{31}$P NMR (162 MHz, CD$_3$CN) δ=28.68; IR (neat) ṽ=690, 717, 737, 751, 852, 964, 996, 1034, 1048, 1170, 1279, 1437, 1478, 1505, 1594, 1615, 3055, 3079 cm$^1$; HRMS calcd. for C$_{18}$H$_{16}$NAuClFP: 528.035295. found: 528.035127.

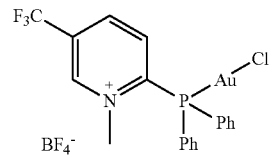

Compound 33

Prepared from 16 (100 mg, 0.23 mmol) and AuCl.SMe$_2$ (68 mg, 0.23 mmol) following the general procedure. White solid (151 mg, 99%).

$^1$H NMR (300 MHz, CD$_3$CN) δ=9.38 (s, 1H), 8.80-8.71 (m, 1H), 7.90-7.67 (m, 11H), 4.47 (s, 3H); $^{13}$C NMR (75 MHz, CD$_3$CN) δ=153.75 (d, J$_{C-P}$=46.8 Hz), 150.38 (d, J$_{C-P}$=2.5 Hz), 143.92 (td, J$_{C-P}$=6.1, J$_{C-F}$=3.0 Hz), 136.42 (d, J$_{C-P}$=15.7 Hz), 136.41, 135.62 (d, J$_{C-P}$=2.7 Hz), 133.42-131.99 (dq, J$_{C-P}$=37.1 Hz, J$_{C-F}$=1.6 Hz), 131.74 (d, J$_{C-P}$=13.0 Hz), 123.16 (d, J$_{C-P}$=64.7 Hz), 122.07 (q, J$_{C-F}$=273.3 Hz), 50.82 (d, J$_{C-P}$=11.3 Hz); $^{19}$F NMR (282 MHz, CDCl$_3$) δ=−63.71, −151.49, −151.54; $^{31}$P NMR (121 MHz, CD$_3$CN) δ=31.54; IR (neat) ṽ=691, 705, 715, 752, 873, 892, 996, 1053, 1118, 1162, 1200, 1280, 1334, 1393, 1440, 1481, 1510, 1590, 1634, 3092 cm$^{-1}$; HRMS calcd. for C$_{20}$H$_{18}$F$_3$NP: 578.032104. found: 578.032257.

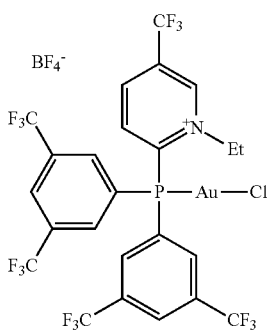

Compound 34

Prepared from 19 (73 mg, 0.1 mmol) and AuCl.SMe$_2$ (30 mg, 0.1 mmol) following the general procedure. White solid (37 mg, 38%).

$^1$H NMR (400 MHz, CD$_3$CN) δ=9.44 (s, 1H), 8.78 (d, J=8.4 Hz, 1H), 8.45 (s, 2H), 8.30 (d, J=13.7 Hz, 4H), 7.92 (t, J=7.7 Hz, 1H), 4.83 (qd, J=7.0, 0.9 Hz, 2H), 1.64 (t, J=7.2 Hz, 3H); $^{13}$C NMR (101 MHz, CD$_3$CN) δ=149.17, 144.40 (dd, J$_{C-P}$=5.9 Hz, J$_{C-F}$=3.0 Hz), 138.49 (d, J$_{C-P}$=9.6 Hz), 137.13 (d, J$_{C-P}$=3.1 Hz), 136.96 (d, J$_{C-P}$=3.1 Hz), 134.10 (qd, J$_{C-P}$=34.5 Hz, J$_{C-P}$=13.2 Hz), 134.00 (d, J$_{C-P}$=37.3 Hz), 129.97 (d, J$_{C-P}$=2.4 Hz), 126.61 (d, J$_{C-P}$=60.9 Hz), 123.66 (q, J$_{C-F}$=273.1 Hz), 122.00 (q, J$_{C-F}$=273.6 Hz), 58.97 (d, J$_{C-P}$=12.7 Hz), 16.49; $^{19}$F NMR (282 MHz, CDCl$_3$) δ=−63.49, −63.59, −151.86, −151.90; $^{31}$P NMR (162 MHz, CD$_3$CN) δ=32.38; IR (neat) ṽ=681, 699, 718, 731, 742, 764, 847, 866, 899, 927, 997, 1032, 1058, 1097, 1123, 1186, 1280, 1337, 1358, 1405, 1447, 1505, 1630, 3093 cm$^{-1}$; HRMS calcd. for C$_{24}$H$_{14}$NAuClF$_{15}$P: 863.997295. found: 863.997181.

As shown above, the inventors outlined herein the preparation of a new family of bench stable cationic phosphines, i.e. pyridiniophosphines, through a short and highly modular synthesis. The inventors have found out that their electronic properties evidenced weak σ-donor and quite strong π-acceptor character when used as ancillary ligands. These attributes confer a substantially enhanced π-acidity to the Pt(II) and Au(I) complexes thereof derived and, as result, the compounds depict an improved ability to activate alkynes towards nucleophilic attack. This superior performance has been demonstrated along several mechanistically diverse Pt(II) and Au(I) catalysed transformations. Thus, when used as ligands, the inventive compounds depict excellent π-acceptor properties and, as consequence, a remarkable ability to enhance the Lewis acidity of the metals they coordinate. The beneficial effects of these properties in homogeneous catalysis have been demonstrated along three mechanistically diverse Pt(II)- and Au(I)-catalysed reactions.

The invention claimed is:

1. N-substituted pyridiniophosphine of the general formula (I):

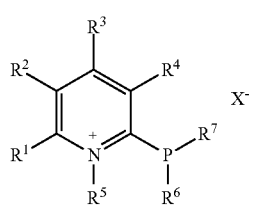

(I)

wherein

R$^1$, R$^2$, R$^3$ and R$^4$ are identical or different and each represent hydrogen, halogen, a linear, cyclic or branched C$_1$-C$_{20}$-alkyl, -alkenyl group or -alkynyl group or C$_5$-C$_{14}$-aryl or -heteroaryl group, which can have suitable substituents selected from halogen, =O, —OH, —OR, —NH$_2$, —NHR, —NR$_2$, aryl or heteroaryl, or at least one of R$^1$, R$^2$, R$^3$ and R$^4$ is bound to the pyridinio ring via —O— or —NR—, or at least two of R$^1$, R$^2$, R$^3$ and R$^4$ can form a linear or branched C$_4$ to C$_{12}$ alkyl ring, which can comprise at least one unsaturated bond and which can have suitable substituents selected from halogen, =O, —OH, —OR, —NH$_2$, —NHR, —NR$_2$, aryl or heteroaryl, or at least two of R$^1$, R$^2$, R$^3$ and R$^4$ can form a C$_5$ to C$_{14}$-aromatic or -heteroaromatic ring which can have suitable substituents selected from halogen, —OH, —OR, —NH$_2$, —NHR, —NR$_2$, aryl or heteroaryl;

R$^5$ represents a linear, cyclic or branched C$_1$-C$_{20}$-alkyl group or C$_5$-C$_{14}$-aryl or -heteroaryl group, which can have suitable substituents selected from halogen, =O, —OH, —OR, —NH$_2$, —NHR, —NR$_2$, aryl or heteroaryl;

R$^6$ and R$^7$ each represent a saturated or unsaturated, linear, branched or cyclic C$_1$-C$_{20}$-alkyl group or or C$_5$-C$_{14}$-aryl or -heteroaryl group, which can have suitable substituents selected from halogen, —OH, —OR, —NH$_2$, —NHR, —NR$_2$, aryl or heteroaryl, or R$^6$ and R$^7$ can form a C$_4$ to C$_{20}$ ring which can comprise at least one unsaturated bond or an aromatic or heteroaromatic ring which can have suitable substituents selected from halogen, —OH, —OR, —NH$_2$, —NHR, —NR$_2$, aryl or heteroaryl, R represents a C$_1$-C$_{20}$-alkyl group or C$_5$-C$_{14}$-aryl or -heteroaryl group which can have suitable substituents selected from halogen, =O, —OH, —OR, —NH$_2$, —NHR, —NR$_2$, aryl or heteroaryl, and X$^-$ is an anion.

2. N-substituted pyridiniophosphine of the general formula (I) according to claim 1, wherein R$^1$, R$^3$ and R$^4$ each represent hydrogen and R$^2$ represents halogen, a linear, cyclic or branched C$_1$-C$_{20}$-alkyl, -alkenyl or -alkynyl group or C$_5$-C$_{14}$-aryl or -heteroaryl group, which can have suitable substituents selected from halogen, =O, —OH, —OR, —NH$_2$, —NHR, —NR$_2$, aryl or R$^2$ is bound to the pyridinio ring via —O— or —NR—; and R$^5$, R$^6$, R$^7$, R and X$^-$ have the meaning as given in claim 1.

3. N-substituted pyridiniophosphine of the general formula (I) according to claim 1, wherein X$^-$ is an anion selected from Cl$^-$, Br$^-$, I$^-$, PF$_6^-$, SbF$_6^-$, BF$_4^-$, ClO$_4^-$, F$_3$CCOO$^-$, Tf$_2$N$^-$, (Tf=trifluoromethanesulfonyl), TfO$^-$, tosyl, [B[3,5-(CF$_3$)$_2$C$_6$H$_3$]$_4$]$^-$, [B(C$_6$F$_5$)$_4$]$^-$, and [Al(OC(CF$_3$)$_3$)$_4$]$^-$.

4. A process for the preparation of N-substituted pyridiniophosphine with the general formula I:

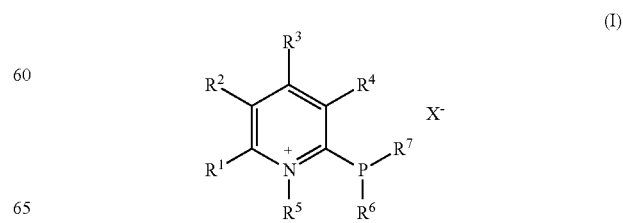

(I)

wherein

R¹, R², R³ and R⁴ are identical or different and each represent hydrogen, halogen, a linear, cyclic or branched $C_1$-$C_{20}$-alkyl, -alkenyl group or -alkynyl group or $C_5$-$C_{14}$-aryl or -heteroaryl group, which can have suitable substituents selected from halogen, =O, —OH, —OR, —NH₂, —NHR, —NR₂, aryl or heteroaryl, or at least one of R², R³ and R⁴ is bound to the pyridinio ring via —O— or —NR—, or at least two of R¹, R², R³ and R⁴ can form a linear or branched $C_4$-$C_{12}$-alkyl ring, which can comprise at least one unsaturated bond and which can have suitable substituents selected from halogen, =O, —OH, —OR, —NH₂, —NHR, —NR₂, aryl or heteroaryl, or at least two of R¹, R², R³ and R⁴ can form a $C_5$-$C_{14}$-aromatic or -heteroaromatic ring which can have suitable substituents selected from halogen, —OH, —OR, —NH₂, —NHR, —NR₂, aryl or heteroaryl;

R⁵ represents a linear, cyclic or branched $C_1$-$C_{20}$-alkyl group or $C_5$-$C_{14}$-aryl or -heteroaryl group, which can have suitable substituents selected from halogen, =O, —OH, —OR, —NH₂, —NHR, —NR₂, aryl or heteroaryl;

R⁶ and R⁷ each represent a saturated or unsaturated, linear, branched or cyclic $C_1$-$C_{20}$-alkyl group or $C_5$-$C_{14}$-aryl or -heteroaryl group, which can have suitable substituents selected from halogen, —OH, —OR, —NH₂, —NHR, —NR₂, aryl or heteroaryl, or R⁶ and R⁷ can form a $C_4$ to $C_{20}$ ring which can comprise at least one unsaturated bond or an aromatic or heteroaromatic ring which can have suitable substituents selected from halogen, —OH, —OR, —NH₂, —NHR, —NR₂, aryl or heteroaryl;

R represents a $C_1$-$C_{20}$-alkyl group or $C_5$-$C_{14}$-aryl or -heteroaryl group which can have suitable substituents selected from halogen, =O, —OH, —OR, —NH₂, —NHR, —NR₂, aryl or heteroaryl, and X⁻ is an anion, in which process a pyridinio-compound salt with the general formula II:

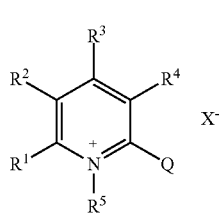

(II)

wherein R¹, R², R³, R⁴, R⁵ and X⁻ are defined as above and Q represents a leaving group, is reacted with a phosphine of the general formula III:

HPR⁶R⁷     (III)

in which R⁶ and R7 are defined as above.

5. A metal complex comprising as a ligand a N-substituted pyridiniophosphine of the general formula (I) according to claim 1.

6. Metal complex of the general formula (IV)

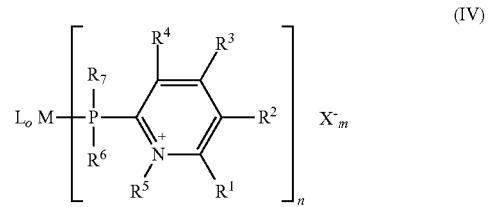

(IV)

wherein

R¹, R², R³ and R⁴ are identical or different and each represent hydrogen, halogen, a linear, cyclic or branched $C_1$-$C_{20}$-alkyl, -alkenyl group or -alkynyl group or $C_5$-$C_{14}$-aryl or -heteroaryl group, which can have suitable substituents selected from halogen, =O, —OH, —OR, —NH₂, —NHR, —NR₂, aryl or heteroaryl, or at least one of R¹, R², R³ and R⁴ is bound to the pyridinio ring via —O— or —NR—, or at least two of R¹, R², R³ and R⁴ can form a linear or branched $C_4$-$C_{12}$-alkyl ring, which can comprise at least one unsaturated bond and which can have suitable substituents selected from halogen, =O, —OH, —OR, —NH₂, —NHR, —NR₂, aryl or heteroaryl, or at least two of R¹, R², R³ and R⁴ can form a $C_5$-$C_{14}$-aromatic or -heteroaromatic ring which can have suitable substituents selected from halogen, —OH, —OR, —NH₂, —NHR, —NR₂, aryl or heteroaryl;

R⁵ represents a linear, cyclic or branched $C_1$-$C_{20}$-alkyl group or $C_5$-$C_{14}$-aryl or -heteroaryl group, which can have suitable substituents selected from halogen, =O, —OH, —OR, —NH₂, —NHR, —NR₂, aryl or heteroaryl;

R⁶ and R⁷ each represent a saturated or unsaturated, linear, branched or cyclic $C_1$-$C_{20}$-alkyl group or $C_5$-$C_{14}$-aryl or -heteroaryl group, which can have suitable substituents selected from halogen, —OH, —OR, —NH₂, —NHR, —NR₂, aryl or heteroaryl; or R⁶ and R⁷ can form a $C_4$ to $C_{20}$ ring which can comprise at least one unsaturated bond or an aromatic or heteroaromatic ring which can have suitable substituents selected from halogen, —OH, —OR, —NH₂, —NHR, —NR₂, aryl or heteroaryl, R represents a $C_1$-$C_{20}$-alkyl group or $C_5$-$C_{14}$-aryl or -heteroaryl group which can have suitable substituents selected from halogen, =O, —OH, —OR, —NH₂, —NHR, —NR₂, aryl or heteroaryl, and X⁻ is an anion, M represents a metal atom, L represents a ligand which can be also cationic, neutral or anionic and can be the same or different if more than one L is coordinated to the metal, and m can be 1, 2 or 3, n can be 1, 2 or 3, o can be an integer from 1 to 5, and m, n and o are chosen, depending on the metal atom, to obtain a metal complex.

7. The metal complex as claimed in claim 6, wherein the ligand L can be chosen from halogen, CN, CO, alkenes, cycloalkenes and/or alkynes, arenes, nitriles, phosphines, amines, pyridines or carboxylates.

8. The metal complex as claimed in claim 6, wherein M is selected from Ag, Au, Ru, Rh, Pd, Os, Ir and Pt.

9. An organic synthesis process comprising conducting a chemical reaction in the presence of a catalyst, wherein the catalyst is the metal complex as claimed in claim 6.

10. N-substituted pyridiniophosphine of the general formula (I) according to claim 1, wherein heteroaryl is selected from among the groups 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, 1,3-benzodioxol-5-yl, 1,4-benzodioxan-6-yl, 2,1,3-benzothiadiazol-4- or -5-yl or 2,1,3-benzoxadiazol-5-yl, each of which heteroaryl groups is optionally substituted as provided in claim 1.

* * * * *